(12) United States Patent
Rajagopalan et al.

(10) Patent No.: US 9,157,730 B2
(45) Date of Patent: Oct. 13, 2015

(54) PECVD PROCESS

(71) Applicant: Applied Materials, Inc., Santa Clara, CA (US)

(72) Inventors: Nagarajan Rajagopalan, Santa Clara, CA (US); Xinhai Han, Fremont, CA (US); Michael Tsiang, Fremont, CA (US); Masaki Ogata, San Jose, CA (US); Zhijun Jiang, Sunnyvale, CA (US); Juan Carlos Rocha-Alvarez, San Carlos, CA (US); Thomas Nowak, Cupertino, CA (US); Jianhua Zhou, Campbell, CA (US); Ramprakash Sankarakrishnan, Santa Clara, CA (US); Ganesh Balasubramanian, Sunnyvale, CA (US); Amit Kumar Bansal, Sunnyvale, CA (US); Jeongmin Lee, Santa Clara, CA (US); Todd Egan, Fremont, CA (US); Edward Budiarto, Fremont, CA (US); Dmitriy Panasyuk, Santa Clara, CA (US); Terrance Y. Lee, Oakland, CA (US); Jian J. Chen, Fremont, CA (US); Mohamad A. Ayoub, Los Gatos, CA (US); Heung Lak Park, San Jose, CA (US); Patrick Reilly, Dublin, CA (US); Shahid Shaikh, Santa Clara, CA (US); Bok Hoen Kim, San Jose, CA (US); Sergey Starik, Kiev (UA)

(73) Assignee: APPLIED MATERIALS, INC., Santa Clara, CA (US)

( * ) Notice: Subject to any disclaimer, the term of this patent is extended or adjusted under 35 U.S.C. 154(b) by 6 days.

(21) Appl. No.: 14/056,203

(22) Filed: Oct. 17, 2013

(65) Prior Publication Data

US 2014/0118751 A1     May 1, 2014

Related U.S. Application Data

(60) Provisional application No. 61/761,515, filed on Feb. 6, 2013, provisional application No. 61/738,247, filed on Dec. 17, 2012, provisional application No. 61/719,319, filed on Oct. 26, 2012.

(51) Int. Cl.
*G01B 11/06* (2006.01)
*H01L 21/00* (2006.01)

(52) U.S. Cl.
CPC ............ *G01B 11/0625* (2013.01); *H01L 21/00* (2013.01); *G01B 11/0683* (2013.01)

(58) Field of Classification Search
CPC ............... G01B 11/0625; G01B 11/06; G01B 11/0683; G01B 11/02; G01N 21/8422; G01N 21/9501; G01N 21/211; G01N 2121/55
USPC .................................................. 356/630–632
See application file for complete search history.

(56) References Cited

U.S. PATENT DOCUMENTS 5,452,091 A * 9/1995 Johnson ......................... 356/445
6,091,485 A * 7/2000 Li et al. ............................ 356/73

(Continued)

FOREIGN PATENT DOCUMENTS

KR      100716266 B1    5/2007
KR      100744528 B1    7/2007

(Continued)

OTHER PUBLICATIONS

PCT Notification of Transmittal of the International Search Report and the Written Opinion of the International Searching Authority, or the Declaration for International Application No. PCT/US2013/066443; 11pages; Feb. 24, 2014.

*Primary Examiner* — Hoa Pham
(74) *Attorney, Agent, or Firm* — Patterson & Sheridan, LLP

(57) ABSTRACT

A method of processing a substrate according to a PECVD process is described. Temperature profile of the substrate is adjusted to change deposition rate profile across the substrate. Plasma density profile is adjusted to change deposition rate profile across the substrate. Chamber surfaces exposed to the plasma are heated to improve plasma density uniformity and reduce formation of low quality deposits on chamber surfaces. In situ metrology may be used to monitor progress of a deposition process and trigger control actions involving substrate temperature profile, plasma density profile, pressure, temperature, and flow of reactants.

18 Claims, 19 Drawing Sheets

(56) References Cited

U.S. PATENT DOCUMENTS

| | | |
|---|---|---|
| 6,621,459 B2 | 9/2003 | Webb et al. |
| 6,970,255 B1 * | 11/2005 | Spady et al. ............ 356/616 |
| 7,009,281 B2 | 3/2006 | Bailey, III et al. |
| 7,019,844 B2 | 3/2006 | Venugopal et al. |
| 7,099,013 B2 | 8/2006 | Katz et al. |
| 7,531,369 B2 | 5/2009 | Venugopal |
| 7,683,289 B2 | 3/2010 | Dhindsa et al. |
| 7,708,859 B2 | 5/2010 | Huang et al. |
| 8,017,527 B1 | 9/2011 | Dhas et al. |
| 8,137,467 B2 | 3/2012 | Meinhold et al. |
| 8,271,121 B2 | 9/2012 | Venugopal et al. |
| 8,299,390 B2 | 10/2012 | Dhindsa et al. |
| 8,313,611 B2 | 11/2012 | Larson |
| 8,358,416 B2 | 1/2013 | Venugopal et al. |
| 8,461,674 B2 | 6/2013 | Gaff et al. |
| 8,546,732 B2 | 10/2013 | Singh |
| 8,563,619 B2 | 10/2013 | Dhindsa et al. |
| 8,624,168 B2 | 1/2014 | Gaff et al. |
| 8,637,794 B2 | 1/2014 | Singh et al. |
| 8,673,080 B2 | 3/2014 | Meinhold et al. |
| 8,709,551 B2 | 4/2014 | Fox et al. |
| 2004/0135081 A1 | 7/2004 | Larson et al. |
| 2007/0151517 A1 | 7/2007 | Baik et al. |
| 2009/0161244 A1 * | 6/2009 | Hirose et al. ............ 360/31 |
| 2009/0168079 A1 * | 7/2009 | Yang ............ 356/630 |
| 2011/0172974 A1 * | 7/2011 | Ku et al. ............ 703/2 |
| 2011/0236594 A1 | 9/2011 | Haverkamp et al. |
| 2013/0072035 A1 | 3/2013 | Gaff et al. |
| 2013/0126476 A1 | 5/2013 | Marakhtanov et al. |

FOREIGN PATENT DOCUMENTS

| | | |
|---|---|---|
| KR | 100765128 B1 | 10/2007 |
| KR | 20070096248 A | 10/2007 |
| KR | 20070109453 A | 11/2007 |
| KR | 100782292 B1 | 12/2007 |
| KR | 20070119169 A | 12/2007 |
| KR | 20080007828 A | 1/2008 |
| KR | 20080041889 A | 5/2008 |
| KR | 20080041893 A | 5/2008 |
| KR | 100953736 B1 | 4/2010 |
| KR | 20110041709 A | 4/2011 |
| KR | 20110080458 A | 7/2011 |
| KR | 20120021025 A | 3/2012 |
| KR | 20120073839 A | 7/2012 |
| KR | 20120079961 A | 7/2012 |
| KR | 20130053273 A | 5/2013 |
| WO | 2007/131057 A2 | 11/2007 |

* cited by examiner

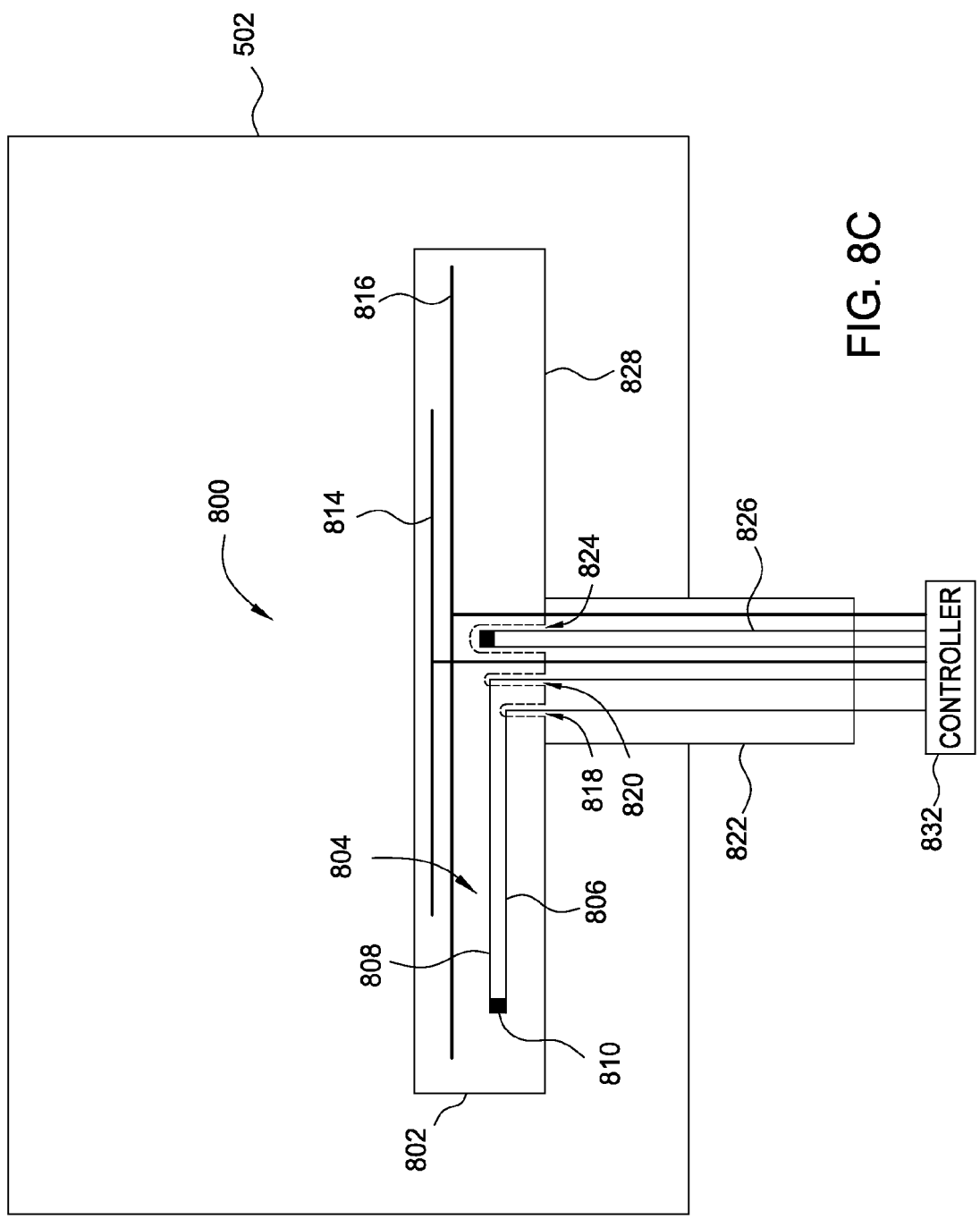

PECVD PROCESS

CROSS-REFERENCE TO RELATED APPLICATIONS

This application claims benefit of U.S. Provisional Patent Application Ser. No. 61/761,515, filed Feb. 6, 2013, U.S. Provisional Patent Application Ser. No. 61/738,247, filed Dec. 17, 2012, and U.S. Provisional Patent Application Ser. No. 61/719,319, filed Oct. 26, 2012, each of which is incorporated herein by reference.

FIELD

Embodiments described herein relate to processes and apparatus for performing plasma deposition on a substrate. More specifically, embodiments described herein relate to plasma deposition processes and apparatus for forming layers having extreme uniformity of composition and thickness.

BACKGROUND

The semiconductor industry has grown according to Moore's Law for the last fifty years. Moore's Law roughly holds that the number of transistors on an integrated circuit doubles about every two years. Inherent in this formulation of is the limitation that the progression of transistor density is two-dimensional, and that at some point physics imposes a limit on how small devices can be.

Recently, manufacturers have developed processes that extend device structures into the third dimension to increase processing capability. Such devices generally feature large numbers of material layers deposited sequentially on a substrate. In some cases, over 100 layers may be formed. When so many layers are formed sequentially, non-uniformities in each layer can multiply, resulting in unusable structures. Current layer formation processes and apparatus typically produce non-uniformities that are not suitable for three-dimensional structures. Thus, new processes and apparatus are needed for forming extremely uniform layers on a substrate.

SUMMARY

Embodiments described herein provide a method of processing a substrate that includes disposing the substrate on a substrate support in a plasma processing chamber, providing a deposition precursor to the processing chamber, forming a plasma from the deposition precursor, depositing a layer on the substrate from the plasma, adjusting a density profile of the plasma by a process comprising changing impedance of a path to ground, and adjusting a temperature profile of the substrate by applying a first energy flux to a first portion of the substrate and a second energy flux to a second portion of the substrate, wherein the first portion is different from the second portion and the first energy flux is different from the second energy flux.

Also described is a method of processing a substrate, including disposing the substrate on a substrate support in a plasma processing chamber, providing a deposition precursor to the processing chamber, forming a plasma from the deposition precursor, depositing a layer on the substrate from the plasma, monitoring a rate of deposition of the layer at a plurality of locations on the substrate by analyzing light reflected from the substrate at the plurality of locations, and adjusting a density profile of the plasma based on the analysis of the reflected light by a process comprising changing impedance of a first path to ground.

Also described is a method of processing a substrate, including disposing the substrate on a substrate support in a plasma processing chamber, providing a deposition precursor to the processing chamber, forming a plasma from the deposition precursor, depositing a layer on the substrate from the plasma, monitoring a rate of deposition of the layer at a plurality of locations on the substrate by analyzing light reflected from the substrate at the plurality of locations, and adjusting a temperature profile of the substrate based on the analysis of the reflected light by applying a first energy flux to a first portion of the substrate and a second energy flux to a second portion of the substrate, wherein the first portion is different from the second portion and the first energy flux is different from the second energy flux.

BRIEF DESCRIPTION OF THE DRAWINGS

FIG. 8C is a schematic cross-sectional view of a chamber having the multi-zone substrate support of FIG. 8B disposed therein.

DETAILED DESCRIPTION

Extremely uniform, high quality, device layers may be formed on a substrate in a plasma process by controlling uniformity of gas flow, uniformity of temperature among surfaces of the processing chamber, temperature profile of the substrate, and plasma density profile at various locations of the substrate surface. Plasma density profile and temperature profile can be adjusted together to achieve a desired deposition rate profile across a substrate surface. Temperature uniformity of chamber surfaces can be adjusted to provide uniform concentration of reactive species and to control and/or minimize deposition on chamber surfaces.

Figure 1:
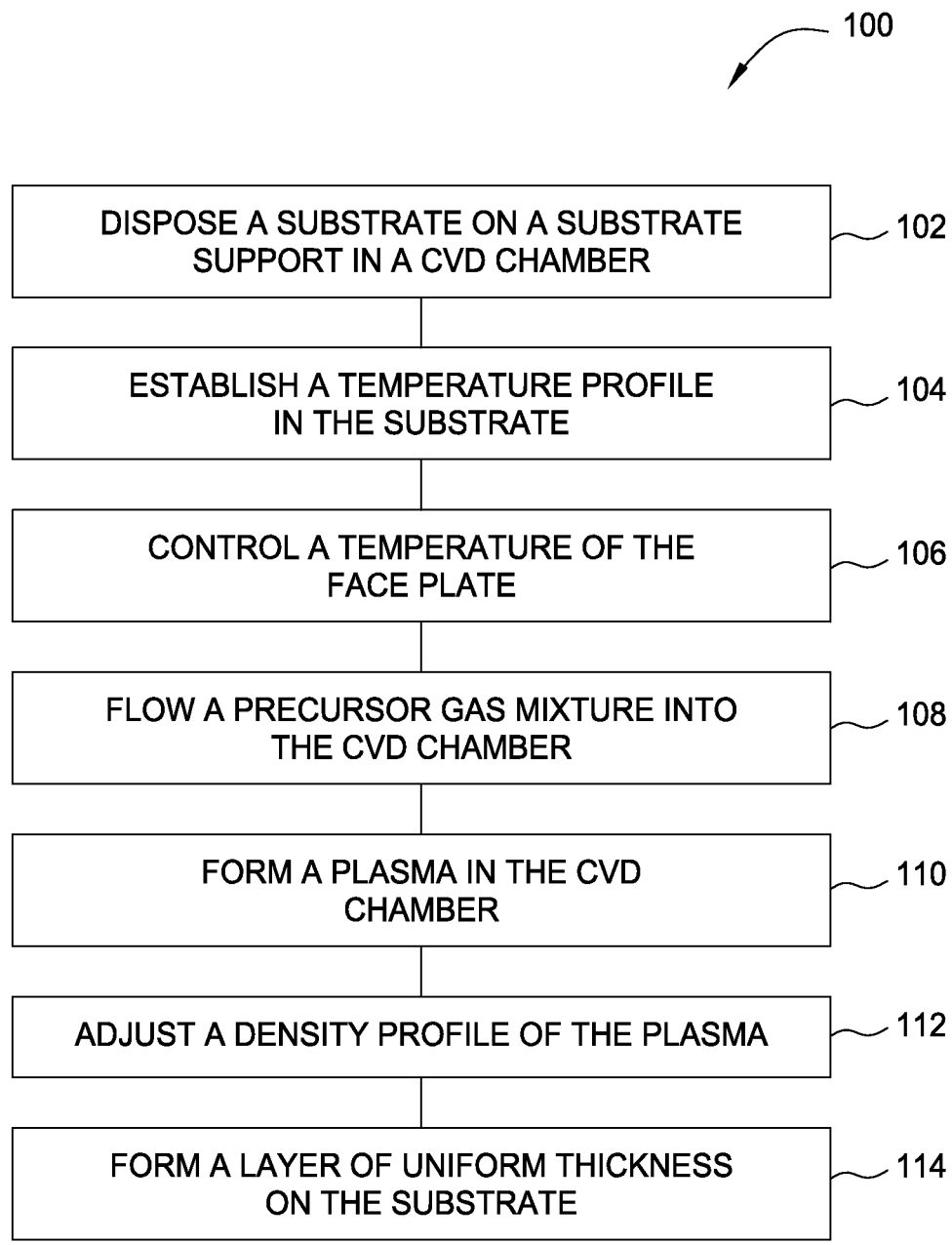
FIG. 1 is a flow diagram summarizing a method according to one embodiment.

A method 100 of forming a layer of uniform thickness and composition on a substrate is summarized in the flow diagram of FIG. 1. At 102, a substrate is disposed on a substrate support in a CVD chamber.

At 104, a temperature profile is established within the substrate. This may be done by heating different parts of the substrates at different rates, for example using a zoned heater. A two-zone heater may be used and a temperature offset between the zones may be from about −50° C. to about +50° C. The substrate temperature may be from about 300° C. to about 800° C., such as between about 400° C. and about 650° C., depending on the material being deposited.

At 106, a face plate temperature is selected and controlled. The face plate is the surface of the chamber lid that is exposed to the processing environment and faces the substrate support. Controlling the face plate temperature promotes temperature uniformity in the processing region of the chamber near the face plate, improving compositional uniformity of the reaction gas mixture as it exits the face plate into the processing region. Face plate temperature may be controlled by thermally coupling a heating element to the face plate. This may be done by direct contact between the heating element and the face plate, or may be by conduction through another member. The face plate temperature may be between about 100° C. and about 300° C.

At 108, a precursor gas mixture is provided to the chamber through the temperature controlled face plate. The gas mixture may be any suitable CVD precursor mixture, such as a silicon (polysilicon or amorphous silicon), silicon oxide, silicon nitride, or silicon oxynitride precursor mixture. Dopant precursors such as boron compounds, phosphorus compounds, and/or arsenic compounds may be included. The following flow rate ranges apply for a chamber sized for 300 mm substrates. Appropriate scaling may be used for chambers sized for other substrates. A silicon precursor such as silane may be provided at a flow rate between about 20 sccm and about 2,000 sccm. TEOS may be provided at a flow rate between about 20 mgm and about 5,000 mgm. An oxygen precursor such as $N_2O$, $O_2$, $O_3$, $H_2O$, CO, or $CO_2$ may be provided at a flow rate between about 1,000 sccm and about 20,000 sccm. A nitrogen precursor such as $N_2$, $N_2O$, $NH_3$, or $H_2N_2$, or a substituted variant thereof, or any mixture of the foregoing nitrogen species, may be provided at a flow rate between about 200 sccm and about 50,000 sccm. A carbon precursor such as a hydrocarbon, for example methane, may be included to add carbon to the layer. Dopants precursors such as trimethylborane (TMB), diborane ($B_2H_6$), phosphine ($PH_3$), arsine ($AsH_3$), and substituted phosphines and arsines, or mixtures thereof, may be provided at flow rates between about 20 sccm and about 3,000 sccm. The dopant precursors may be carried by a carrier gas, or diluted in a dilution gas, for example helium, argon, nitrogen, or hydrogen, or any mixture thereof, flowing at a rate of between about 500 sccm and about 30,000 sccm. Operating pressure between about 0.5 Torr and about 10 Torr is established in the chamber. Spacing between the face plate and the substrate is established between about 200 mils (thousandths of an inch) and 1,100 mils.

At 110, a plasma is formed in the chamber from the precursor gas mixture. The plasma may be formed by capacitive or inductive means, and may be energized by coupling RF power into the precursor gas mixture. The RF power may be a dual-frequency RF power that has a high frequency component and a low frequency component. The RF power is typically applied at a power level between about 50 W and about 1,500 W, which may be all high-frequency RF power, for example at a frequency of about 13.56 MHz, or may be a mixture of high-frequency power and low frequency power, for example at a frequency of about 300 kHz.

At 112, the plasma density profile is adjusted by biasing an electrode coupled to a side wall of the chamber and/or an electrode coupled to the substrate support. Each electrode will typically be controlled to provide impedance for a selected current to flow through the electrode. A resonant tuning circuit is typically coupled to each electrode and to ground, and components for the resonant tuning circuit are selected, with at least one variable component, so the impedance can be adjusted dynamically to maintain the target current flow. The current flow through each electrode may be controlled to a value between about 0 A and about 30 A or between about 1 A and about 30 A.

At 114, a layer is formed on the substrate from the plasma. Depending on the composition of the precursor, the layer may be a silicon layer, for example a polysilicon, microcrystalline silicon, or amorphous silicon layer, which may be doped, a silicon oxide layer, which may be doped, a silicon oxynitride layer, which may be doped, a silicon carbide layer, which may be doped, a silicon oxycarbide layer, which may be doped, a silicon nitrocarbide layer, which may be doped, a silicon nitroxycarbide layer, which may be doped, or a silicon nitride layer, which may be doped. Other layers, for example layers not containing silicon, may also be deposited by selecting appropriate precursors and flow rates.

The layer formed typically has thickness uniformity of 2% or better. In one aspect, the thickness of the deposited layer may vary from an average value by no more than 2%. In another aspect, a standard deviation of the layer thickness is no more than about 2%. This thickness uniformity enables formation of multiple layers, for example up to 150 layers, in a single sequential process in a single chamber, while maintaining a stack structure that is substantially planar, laminar, and parallel.

Uniformity may be further enhanced by controlling temperature of chamber surfaces exposed to the plasma. When chamber surfaces are allowed to float thermally, hot and cold spots can develop that affect plasma density and reactivity in uncontrolled ways. As described above, the face plate of the showerhead may be heated using a resistive heater or thermal fluid disposed in a conduit through a portion of the face plate or otherwise in direct contact or thermal contact with the face plate. The conduit may be disposed through an edge portion of the face plate to avoid disturbing the gas flow function of the face plate. Heating the edge portion of the face plate may be useful to reduce the tendency of the face plate edge portion to be a heat sink within the chamber.

The chamber walls may also be heated to similar effect. Heating the chamber surfaces exposed to the plasma also minimizes deposition, condensation, and/or reverse sublimation on the chamber surfaces, reducing the cleaning frequency of the chamber and increasing mean cycles per clean. Higher temperature surfaces also promote dense deposition that is less likely to produce particles that fall onto a substrate. Thermal control conduits with resistive heaters and/or thermal fluids may be disposed through the chamber walls to achieve thermal control of the chamber walls. Temperature of all surfaces may be controlled by a controller.

Figure 2:
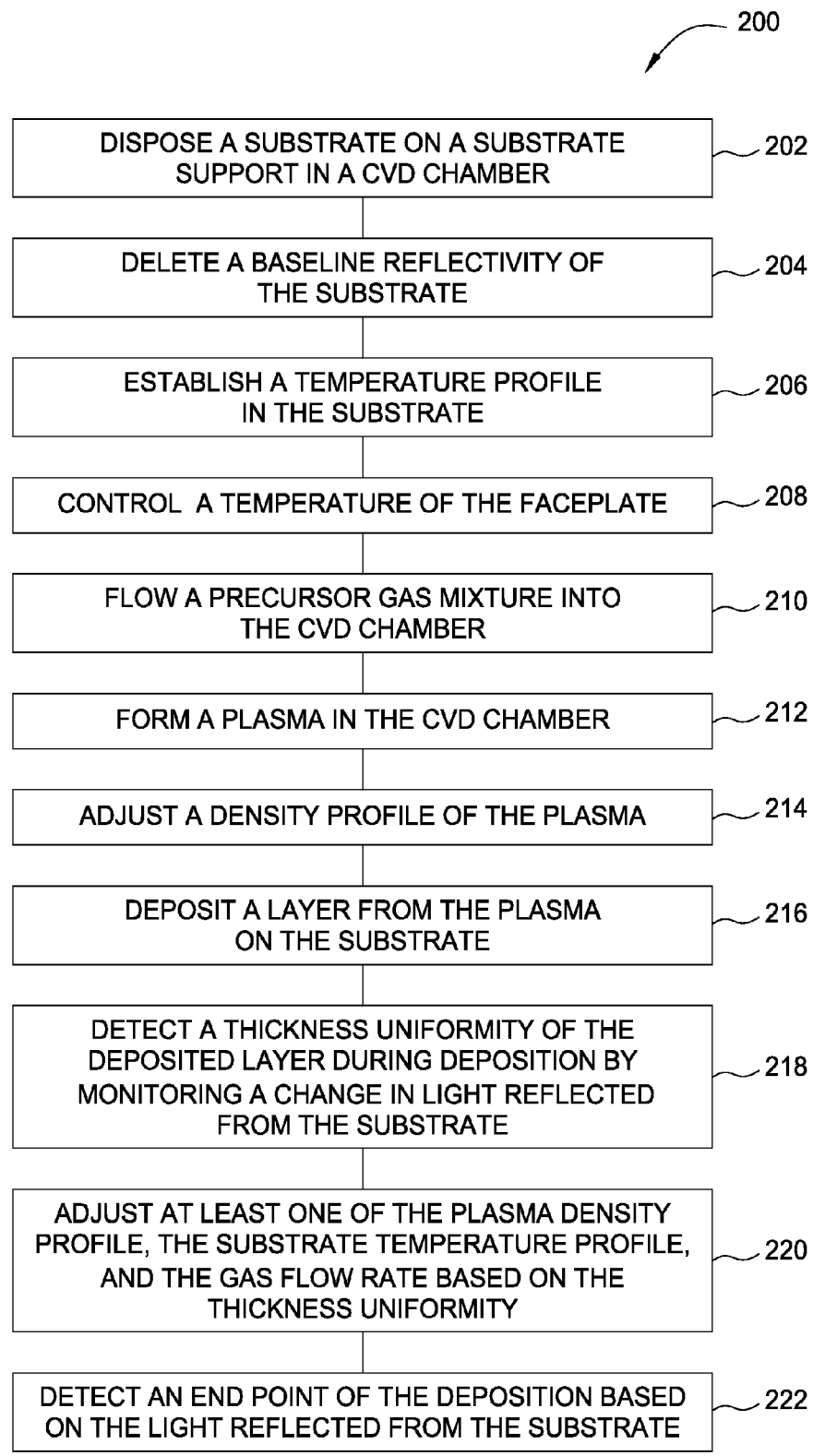
FIG. 2 is a flow diagram summarizing a method according to another embodiment.

A method 200 of forming a layer of uniform thickness and composition on a substrate is summarized in the flow diagram of FIG. 2. The method 200 is similar in many respects to the method 100 of FIG. 1, with the addition of metrology components. At 202, a substrate is disposed on a substrate support in a CVD chamber.

At 204, a baseline reflectivity of the substrate is detected by shining a light on the substrate in the chamber and measuring a spectrum of light reflected by the substrate. An exemplary apparatus for measuring reflectivity of the substrate in situ is described below. Intensity of the light directed to the substrate as a function of wavelength is obtained from spectral analysis of the incident light. Intensity of the light reflected from the substrate as a function of wavelength is obtained from spectral analysis of the reflected light. A ratio of the reflected light intensity to the incident light intensity as a function of wavelength is computed and saved for subsequent processing. An electronic computation device having an electronic memory may be used for analysis of spectral data.

At 206, a temperature profile is established in the substrate, substantially as described above at 104. At 208, a temperature of the face plate is set, as at 106 above. Flow of precursors is established into the CVD chamber at 210, as at 108 above. A plasma is formed in the CVD chamber at 212, as at 110 above. Density profile of the plasma is adjusted and selected at 214, as at 112 above. At 216, a layer is deposited from the plasma onto the substrate, substantially as described above at 114.

At 218, a thickness uniformity of the deposited layer is detected while the layer is being deposited to enable adjustments to control the thickness uniformity. Light reflected from the substrate is monitored as the deposition proceeds, and changes in the reflected light are used to determine thickness. Multiple locations on the substrate are typically monitored to determine changes in thickness at the various locations. The thickness data for the various locations is compared to determine thickness uniformity as the deposition proceeds. Apparatus and algorithms for determining thickness from reflected light is described in more detail below.

At 220, chamber parameters that affect distribution of deposition across the substrate are adjusted based on the thickness uniformity determined at 218 from analysis of the reflected light. At least one of plasma density profile, substrate temperature profile, and gas flow rate are adjusted to control thickness uniformity as deposition of the layer proceeds. Apparatus for adjusting substrate temperature profile and plasma density profile are described in more detail below. Substrate temperature profile is adjusted by changing local energy flux at different locations on the substrate, typically using a substrate support with zoned energy flux. Plasma density profile may be adjusted by applying electrodes around the plasma generation area of the chamber, above the substrate support, and using variable electronic components to adjust impedance of the electrodes independently to change the impedance of various paths to ground for charge carriers in the plasma. Controlling the impedance geometrically directly controls the geometry of plasma density above the substrate support. In this way, more plasma may be attracted toward an edge region of the substrate or pushed toward a central region of the substrate, depending on the desired adjustment.

At 222, reflected light is analyzed to determine a deposition end point based on comparing the overall thickness of the deposited film to a target thickness.

The methods 100 and 200 may be used to form a stack of layers having different composition with repeatable thickness and extreme thickness uniformity. In one embodiment, alternating layers of silicon oxide and silicon nitride may be formed on a silicon substrate in a single process chamber, each layer having a thickness between about 300 Å and about 3,000 Å, and each layer having thickness uniformity, expressed as standard deviation of thickness across the substrate, that is less than about 3%, in some cases as low as 1%. Any number of such layers, for example more than 40 layers, in some cases as many as 125 layers, may be formed sequentially in a single process chamber.

Figure 3:
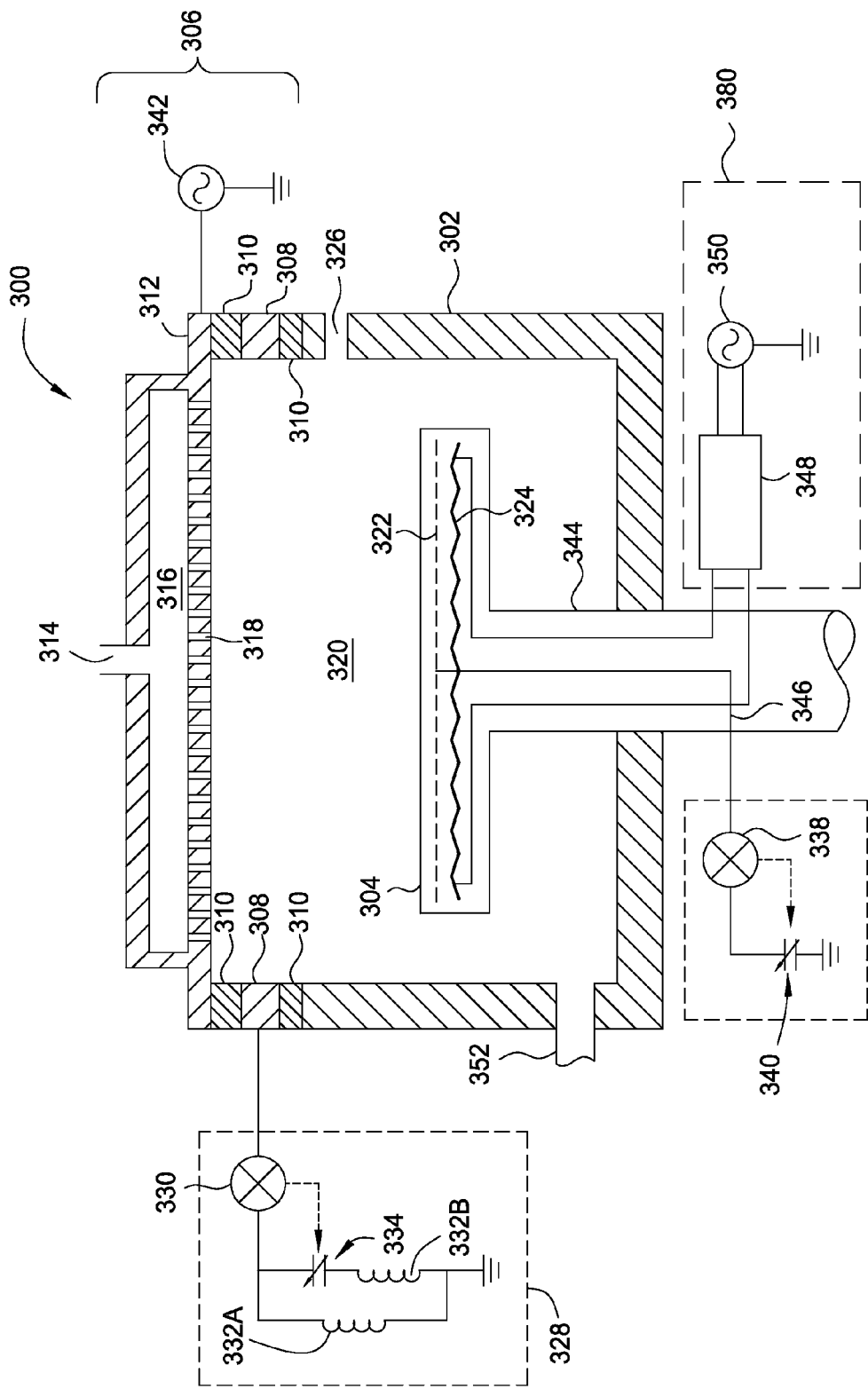
FIG. 3 is a schematic cross-sectional view of an apparatus according to one embodiment.

FIG. 3 is a schematic side view of an inventive apparatus 300 that may be used to practice processes described herein. The processing chamber 300 features a chamber body 302, a substrate support 304 disposed inside the chamber body 302, and a lid assembly 306 coupled to the chamber body 302 and enclosing the substrate support 304 in a processing volume 320. Substrates are provided to the processing volume 320 through an opening 326, which may be conventionally sealed for processing using a door.

An electrode 308 may be disposed adjacent to the chamber body 302 and separating the chamber body 302 from other components of the lid assembly 306. The electrode 308 may be part of the lid assembly 306, or may be a separate side wall electrode. The electrode 308 may be an annular, or ring-like member, and may be a ring electrode. The electrode 308 may be a continuous loop around a circumference of the processing chamber 300 surrounding the processing volume 320, or may be discontinuous at selected locations if desired. The electrode 308 may also be a perforated electrode, such as a perforated ring or a mesh electrode. The electrode 308 may also be a plate electrode, for example a secondary gas distributor.

An isolator 310, which may be a dielectric material such as a ceramic or metal oxide, for example aluminum oxide and/or aluminum nitride, contacts the electrode 308 and separates the electrode 308 electrically and thermally from a gas distributor 312 and from the chamber body 302. The gas distributor 312 features openings 318 for admitting process gas into the processing volume 320. The gas distributor 312 may be coupled to a source of electric power 342, such as an RF generator. DC power, pulsed DC power, and pulsed RF power may also be used.

The gas distributor 312 may be a conductive gas distributor or a non-conductive gas distributor. The gas distributor 312 may also be made of conductive and non-conductive components. For example, a body of the gas distributor 312 may be conductive while a face plate of the gas distributor 312 is non-conductive. In a plasma processing chamber, the gas distributor 312 may be powered, as shown in FIG. 3, or the gas distributor 312 may be coupled to ground.

The electrode 308 may be coupled to a tuning circuit 328 that controls a ground pathway of the processing chamber 300. The tuning circuit 328 comprises an electronic sensor 330 and an electronic controller 334, which may be a variable capacitor. The tuning circuit 328 may be an LLC circuit comprising one or more inductors 332. The tuning circuit 328 may be any circuit that features a variable or controllable impedance under the plasma conditions present in the processing volume 320 during processing. In the embodiment of FIG. 3, the tuning circuit 328 features a first inductor 332A in series with the electronic controller 334 and a second inductor 332B in parallel with the electronic controller 334. The electronic sensor 330 may be a voltage or current sensor, and may be coupled to the electronic controller 334 to afford a degree of closed-loop control of plasma conditions inside the processing volume 320.

A second electrode 322 may be coupled to the substrate support 304. The second electrode 322 may be embedded within the substrate support 304 or coupled to a surface of the substrate support 304. The second electrode 322 may be a plate, a perforated plate, a mesh, a wire screen, or any other distributed arrangement. The second electrode 322 may be a tuning electrode, and may be coupled to a second tuning circuit 136 by a conduit 346, for example a cable having a selected resistance such as 50Ω, disposed in a shaft 344 of the substrate support 304. The second tuning circuit 336 may have a second electronic sensor 338 and a second electronic controller 340, which may be a second variable capacitor. The second electronic sensor 338 may be a voltage or current sensor, and may be coupled to the second electronic controller 340 to provide further control over plasma conditions in the processing volume 320.

A third electrode 324, which may be a bias electrode and/or an electrostatic chucking electrode, may be coupled to the substrate support 304. The third electrode may be coupled to a second source of electric power 350 through a filter 348, which may be an impedance matching circuit. The second source of electric power 350 may be DC power, pulsed DC power, RF power, pulsed RF power, or a combination thereof.

The lid assembly 306 and substrate support 304 of FIG. 3 may be used with any processing chamber for plasma or thermal processing. One example of a plasma processing chamber with which the lid assembly 306 and substrate support 304 may be beneficially used is the PRODUCER® platform and chambers available from Applied Materials, Inc., located in Santa Clara, Calif. Chambers from other manufacturers may also be used with the components described above.

In operation, the processing chamber 300 affords real-time control of plasma conditions in the processing volume 320. A substrate is disposed on the substrate support 304, and process gases are flowed through the lid assembly 306 using an inlet 314 according to any desired flow plan. Gases exit the chamber 300 through an outlet 352 Electric power is coupled to the gas distributor 312 to establish a plasma in the processing volume 320. The substrate may be subjected to an electrical bias using the third electrode 324, if desired.

Upon energizing a plasma in the processing volume 320, a potential difference is established between the plasma and the first electrode 308. A potential difference is also established between the plasma and the second electrode 322. The electronic controllers 334 and 340 may then be used to adjust the flow properties of the ground paths represented by the two tuning circuits 328 and 336. A set point may be delivered to the first tuning circuit 328 and the second tuning circuit 336 to provide independent control of deposition rate and of plasma density uniformity from center to edge. In embodiments where the electronic controllers are both variable capacitors, the electronic sensors may adjust the variable capacitors to maximize deposition rate and minimize thickness non-uniformity independently.

Each of the tuning circuits 328 and 336 has a variable impedance that may be adjusted using the respective electronic controllers 334 and 340. Where the electronic controllers 334 and 340 are variable capacitors, the capacitance range of each of the variable capacitors, and the inductances of the inductors 332A and 332B, are chosen to provide an impedance range, depending on the frequency and voltage characteristics of the plasma, that has a minimum in the capacitance range of each variable capacitor. Thus, when the capacitance of the electronic controller 334 is at a minimum or maximum, impedance of the circuit 328 is high, resulting in a plasma shape that has a minimum areal coverage over the substrate support 304. When the capacitance of the electronic controller 334 approaches a value that minimizes the impedance of the circuit 328, the areal coverage of the plasma grows to a maximum, effectively covering the entire working area of the substrate support 304. As the capacitance of the electronic controller 334 deviates from the minimum impedance setting, the plasma shape shrinks from the chamber walls and areal coverage of the substrate support declines. The electronic controller 340 has a similar effect, increasing and decreasing areal coverage of the plasma over the substrate support as the capacitance of the electronic controller 340 is changed.

The electronic sensors 330 and 338 may be used to tune the respective circuits 328 and 336 in a closed loop. A set point for current or voltage, depending on the type of sensor used, may be installed in each sensor, and the sensor may be provided with control software that determines an adjustment to each respective electronic controller 334 and 340 to minimize deviation from the set point. In this way, a plasma shape can be selected and dynamically controlled during processing. It should be noted that, while the foregoing discussion is based on electronic controllers 334 and 340 that are variable capacitors, any electronic component with adjustable characteristic may be used to provide tuning circuits 328 and 336 with adjustable impedance.

Figure 4:
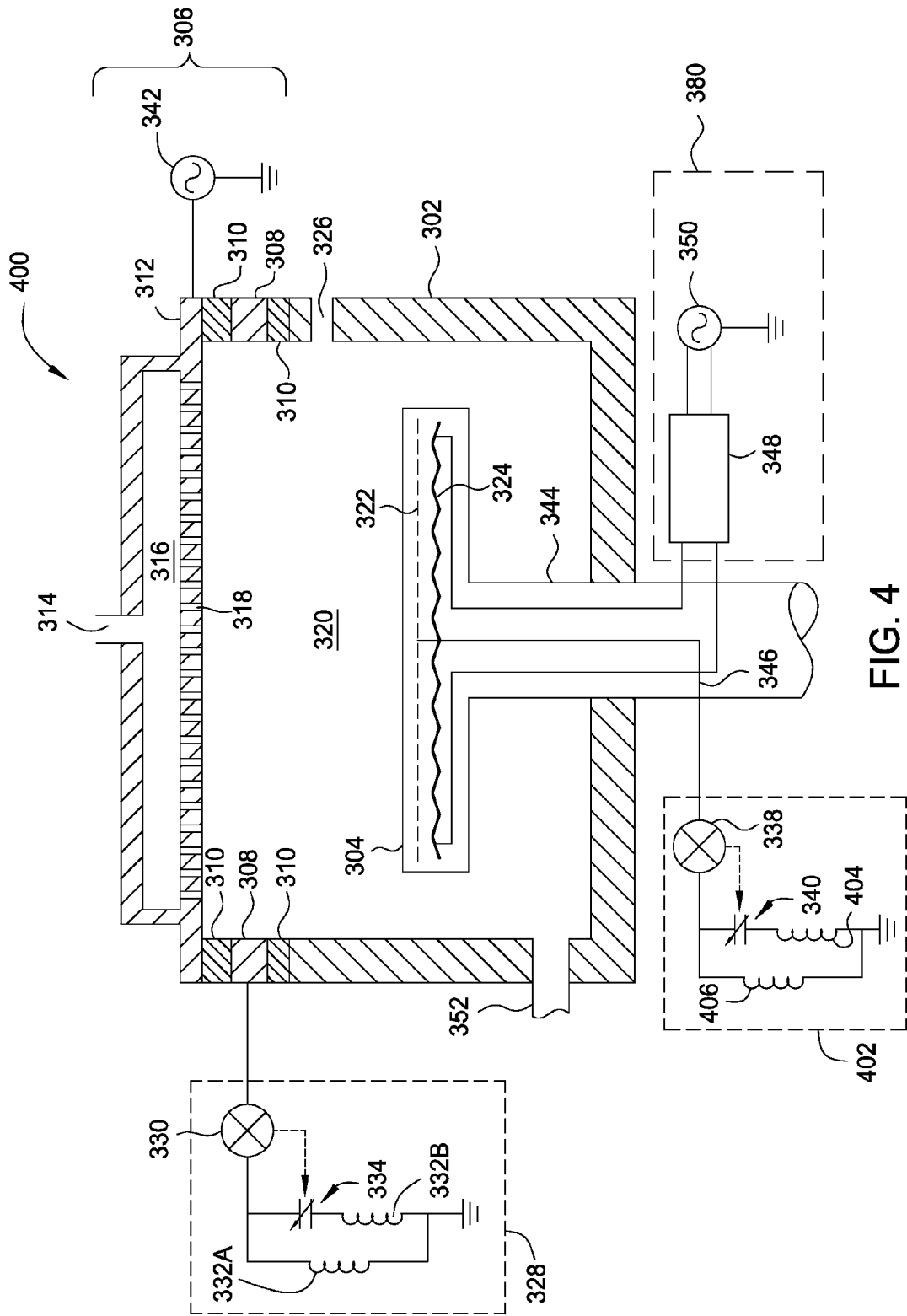
FIG. 4 is a schematic cross-sectional view of an apparatus according to another embodiment.

FIG. 4 is a schematic cross-sectional view of another inventive apparatus 400 that may be used to practice processes described herein. The processing chamber 400 of FIG. 4 is similar in many respects to the processing chamber 300 of FIG. 3, and identical elements are numbered the same in the two figures. The processing chamber 400 features a different tuning circuit 402 coupled to the substrate support 304. The tuning circuit 402 has the same components as the tuning circuit 328, namely the electronic controller 340, the electronic sensor 338, a first inductor 404 in series with the electronic controller 340, and a second inductor 406 in parallel with the electronic controller 340.

The tuning circuit 402 of FIG. 4 works in a manner similar to the tuning circuit 336 of FIG. 3, with different impedance characteristics as the variable component 340 is adjusted. The impedance of the tuning circuit 402 will differ from that of the tuning circuit 336 in a way that depends on the inductances selected for the inductors 404 and 406. Thus, the characteristics of the tuning circuit applied to the substrate support may be adjusted not only by selecting a variable capacitor with a capacitance range that results in an impedance range that is useful in connection with the characteristics of the plasma, but also by selecting inductors to modify the impedance range available using the variable capacitor. As with the tuning circuit 336, the variable capacitor 340 adjusts the impedance of the path to ground through the substrate support, changing the electric potential of the electrode 322 and changing the shape of the plasma in the processing volume 320.

Figure 5A:
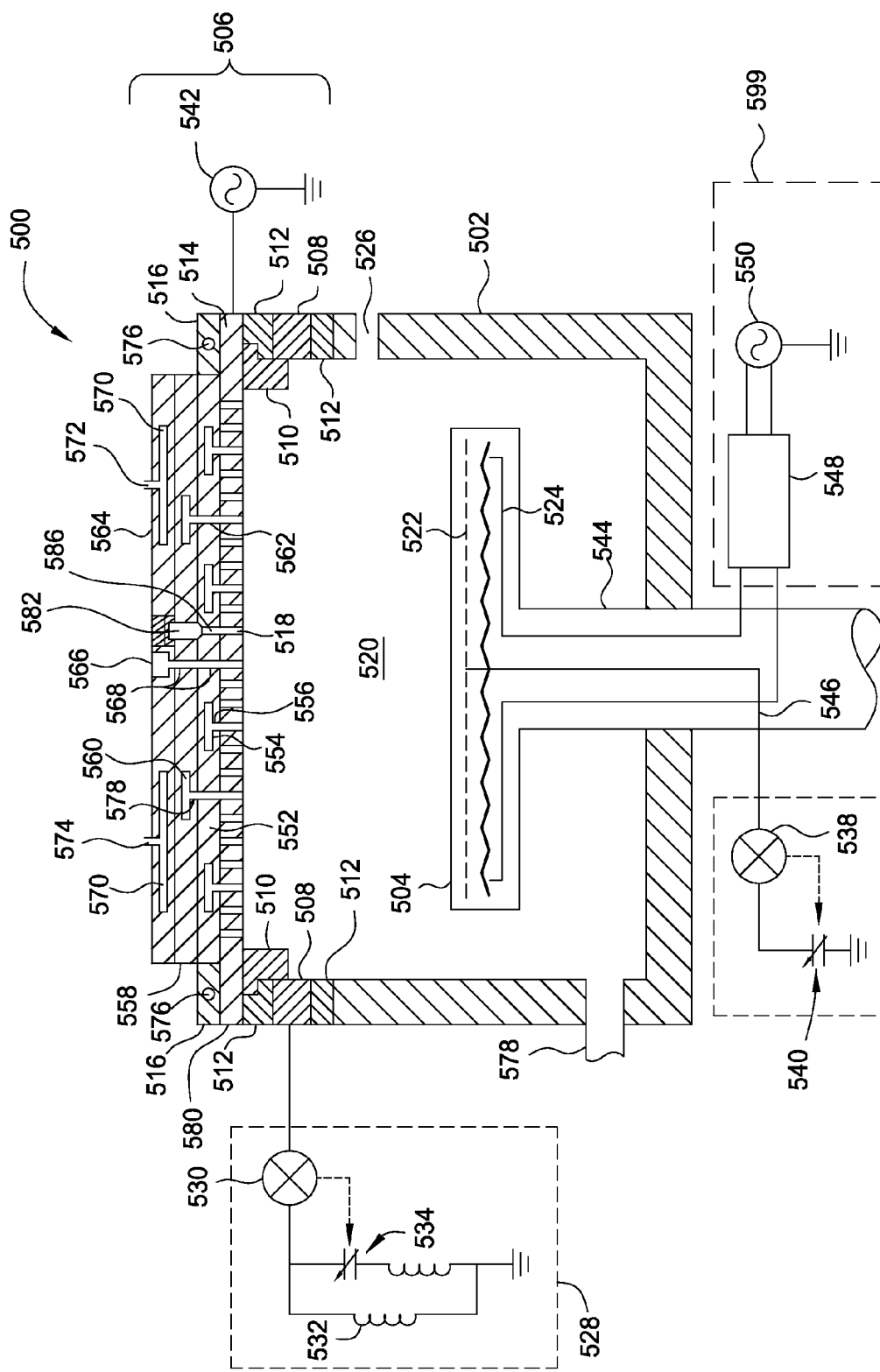
FIG. 5A is a schematic cross-sectional view of an apparatus according to another embodiment.

FIG. 5A is a schematic cross-sectional view of another inventive apparatus 500 that may be used to practice processes described herein. The processing chamber 500 features a chamber body 502, a substrate support 504 disposed inside the chamber body 502, and a lid assembly 506 coupled to the chamber body 502 and enclosing the substrate support 504 in a processing volume 520. Substrates are provided to the processing volume 520 through an opening 526, which may be conventionally sealed for processing using a door.

The lid assembly 506 comprises an electrode 508 disposed adjacent to the chamber body 502 and separating the chamber body 502 from other components of the lid assembly 506. The electrode 508 may be an annular, or ring-like member, and may be a ring electrode. The electrode 508 may be a continuous loop around a circumference of the processing chamber 500 surrounding the processing volume 520, or may be discontinuous at selected locations if desired. A pair of isolators 510 and 512, each of which may be a dielectric material such as a ceramic or metal oxide, for example aluminum oxide and/or aluminum nitride, contacts the electrode 508 and separates the electrode 508 electrically and thermally from a conductive gas distributor 514 and from the chamber body 502.

The isolator 510 may be an internal isolator that is exposed to the processing environment of the processing volume 520, while the isolator 512 may be an external isolator that is not exposed to the processing environment of the processing volume 520. In such an embodiment, the internal isolator may be a material that has higher heat tolerance or heat stability than the external isolator. The internal isolator may comprise a plurality of components fitted together with interfaces that mitigate thermal stresses in the internal isolator. For example, three ceramic rings may make up an internal isolator. If the internal isolator is heat resistant, the external isolator may be a less heat resistant material, such as plastic. If the isolator 510 is an internal isolator provided for stability in the processing environment, the isolator 510 may be extended downward adjacent to the lower instance of the isolator 512 to provide a barrier against the processing environment, if desired. Alternately, the lower instance of the isolator 512 may be replaced with an isolator of the same or similar material as the isolator 510.

In an embodiment where the conductive gas distributor 514 is a conductive face plate, the conductive face plate may be a flat, conductive, plate-like member having a substantially uniform thickness, and a surface of the conductive face plate may be substantially parallel to an upper surface of the substrate support 504. The conductive face plate may be metal, such as aluminum or stainless steel and may be coated in some embodiments with a dielectric material such as aluminum oxide or aluminum nitride.

The conductive gas distributor 514, which may be a conductive face plate, is in thermal contact, and may be in physical contact, with a heater 516. The heater 516 includes a heating element 576, which may be resistive element, such as an electrical conductor designed to radiate heat, or a conductive element, such as a conduit for a heating fluid. The conductive gas distributor 514 features openings 518 for admitting process gas into the processing volume 520. An edge portion 580 of the conductive gas distributor 514 is accessible along the side of the processing chamber 500 to allow coupling of the conductive gas distributor 514 to a source of electric power 542, such as an RF generator. DC power, pulsed DC power, and pulsed RF power may also be used.

A zoned blocker plate comprising a first zoned plate 552 and a second zoned plate 558 contacts the conductive gas distributor 514 and provides multiple gas pathways through the lid assembly 506. While the embodiment shown in FIG. 5A is an example of one configuration of such a zoned blocker plate, other configurations of a zoned blocker plate, including configurations having more than two zoned plates, are conceivable. The first zoned plate 552 has one or more plenums 554 for circulating process gases through a first pathway for distribution to the processing volume 520 through openings 556 in the first zoned plate 552 that are in fluid communication with the openings 518 of the conductive gas distributor 514. The second zoned plate 558 also has one or more plenums 560 for circulating process gases through a second pathway for distribution to the processing volume 520 through openings 578 in the second zoned plate that are in fluid communication with pass-through openings 562 of the first zoned plate 552 and the openings 518 of the conductive gas distributor 514.

A gas cap 564 is disposed in contact with the second zoned plate 558, and provides portals for flowing process gases separately to the plenums 554 in the first zoned plate 552 and the plenums 560 in the second zoned plate 558, allowing the process gases to flow to the processing volume 520 without contacting each other prior to arriving in the processing volume 520. The gas cap 564 also features a portal 566 in fluid communication with a pass-through opening 568 in the second zoned plate 558 and the first zoned plate 552, and with one of the openings 518, for passing process gas directly into the processing volume 520 through a third gas pathway, if desired. The gas cap 564 also features a conduit 570 for circulating a fluid through the gas cap 564. The fluid may be a thermal control fluid, such as a cooling fluid. Water is an example of a cooling fluid that may be used, but other fluids, liquid and solid, may also be used. The thermal control fluid is provided to the conduit 570 through an inlet 572 and is withdrawn from the conduit 570 through an outlet 574. The gas cap 564 is in thermal communication with the first and second zoned plates 552 and 558, and with the conductive gas distributor 514. The heater 516 and the thermally controlled gas cap 564 together provide thermal control for the conductive gas distributor 514 to allow temperature uniformity from edge to center and from substrate to substrate. Gases are evacuated from the processing volume 520 through a portal 578, which may be coupled to a vacuum source (not shown), which may be located at any convenient location along the chamber body, and which may be associated with a pumping plenum, if desired.

The electrode 508 may be coupled to a tuning circuit 528 that controls a ground pathway of the processing chamber 500. The tuning circuit 528 comprises an electronic sensor 530 and an electronic controller 534, which may be a variable capacitor. The tuning circuit 528 may be an LLC circuit comprising one or more inductors 532. The electronic sensor 530 may be a voltage or current sensor, and may be coupled to the electronic controller 534 to afford a degree of closed-loop control of plasma conditions inside the processing volume 520.

A second electrode 522 may be coupled to the substrate support 504. The second electrode 522 may be embedded within the substrate support 504 or coupled to a surface of the substrate support 504. The second electrode 522 may be a plate, a perforated plate, a mesh, a wire screen, or any other distributed arrangement. The second electrode 522 may be a tuning electrode, and may be coupled to a second tuning circuit 536 by a conduit 546, for example a cable having a selected resistance such as 50Ω, disposed in a shaft 544 of the substrate support 504. The second tuning circuit 536 may have a second electronic sensor 538 and a second electronic controller 540, which may be a second variable capacitor. The second electronic sensor 538 may be a voltage or current sensor, and may be coupled to the second electronic controller 540 to provide further control over plasma conditions in the processing volume 520.

A third electrode 524, which may be a bias electrode, may be coupled to the substrate support 504. The third electrode may be coupled to a bias unit 599 comprising a second source of electric power 550 and a filter 548, which may be an impedance matching circuit. The second source of electric power 550 may be DC power, pulsed DC power, RF power, pulsed RF power, or a combination thereof.

The lid assembly 506 and substrate support 504 of FIG. 5A may be used with any processing chamber for plasma or thermal processing. One example of a plasma processing chamber with which the lid assembly 506 and substrate support 504 may be beneficially used is the PRODUCER® platform and chambers available from Applied Materials, Inc., located in Santa Clara, Calif. Chambers from other manufacturers may also be used with the components described above.

In operation, the processing chamber 500 affords real-time control of temperature in the lid assembly 506 and of plasma conditions in the processing volume 520. A substrate is disposed on the substrate support 504, and process gases are flowed through the lid assembly 506 according to any desired flow plan. A temperature set point may be established for the conductive gas distributor, and may be controlled by operation of the heater 516 and by circulation of a cooling fluid through the conduit 570. Electric power may be coupled to the conductive gas distributor 514 to establish a plasma in the processing volume 520. Because the temperature of the conductive gas distributor 514 is controlled, less electric power is dissipated through heating of the conductive gas distributor 514 and other components of the lid assembly 506, and the temperature of the conductive gas distributor 514 is stabilized from center to edge and from substrate to substrate, beginning with the first substrate processed in the processing chamber 500. The substrate may be subjected to an electrical bias using the third electrode 524, if desired.

Upon energizing a plasma in the processing volume 520, a potential difference is established between the plasma and the first electrode 508. A potential difference is also established between the plasma and the second electrode 522. The electronic controllers 534 and 540 may then be used to adjust the flow properties of the ground paths represented by the two tuning circuits 528 and 536. A set point may be delivered to the first tuning circuit 528 and the second tuning circuit 536 to provide independent control of the plasma density uniformity from center to edge and deposition rate. In embodiments where the electronic controllers are both variable capacitors, the electronic sensors may adjust the variable capacitors to maximize deposition rate and minimize thickness non-uniformity independently. A plasma processing chamber may have one of the first or the second electrodes, or both the first and the second electrodes. Likewise, a plasma processing chamber may have one of the first tuning circuit or the second tuning circuit, or both the first and the second tuning circuits.

Each of the tuning circuits 528 and 536 has a variable impedance that may be adjusted using the respective electronic controllers 534 and 540. Where the electronic controllers 534 and 540 are variable capacitors, the capacitance range of each of the variable capacitors, and the inductances of the inductors 532A and 532B, are chosen to provide an impedance range, depending on the frequency and voltage characteristics of the plasma, that has a minimum in the capacitance range of each variable capacitor. Thus, when the capacitance of the electronic controller 534 is at a minimum or maximum, impedance of the circuit 528 is high, resulting in a plasma shape that has a minimum areal coverage over the substrate support. When the capacitance of the electronic controller 534 approaches a value that minimizes the impedance of the circuit 528, the areal coverage of the plasma grows to a maximum, effectively covering the entire working area of the substrate support 504. As the capacitance of the electronic controller 534 deviates from the minimum impedance setting, the plasma shape shrinks from the chamber walls and areal coverage of the substrate support declines. The electronic controller 540 has a similar effect, increasing and decreasing areal coverage of the plasma over the substrate support as the capacitance of the electronic controller 540 is changed.

The electronic sensors 530 and 538 may be used to tune the respective circuits 528 and 536 in a closed loop. A set point for current or voltage, depending on the type of sensor used, may be installed in each sensor, and the sensor may be provided with control software that determines an adjustment to each respective electronic controller 534 and 540 to minimize deviation from the set point. In this way, a plasma shape can be selected and dynamically controlled during processing. It should be noted that, while the foregoing discussion is based on electronic controllers 534 and 540 that are variable capacitors, any electronic component with adjustable characteristic may be used to provide tuning circuits 528 and 536 with adjustable impedance.

The chamber 500 in FIG. 5A also has an optical metrology device 582 disposed in the lid assembly 506. The optical metrology device 582 is typically housed in the second zoned plate 558 and seats in the first zoned plate 552. A different number of plates may be used in the lid assembly 506, if desired. The optical metrology device 582 is typically housed in the first plate beneath the gas cap 564, for ease of access. The optical metrology device 582 is in optical alignment with an opening 586 through the first zoned plate 552. The opening 586 is in alignment and optical registration with a gas flow opening 518 of the conductive gas distributor 514. Typically, openings of this type are provided through all plates between the optical metrology device 582 and the conductive gas distributor 514. The openings 518 of the conductive gas distributor 514 are sized for gas flow uniformity. The optical metrology device 582 produces a light beam that is sized to travel through one of the openings 518 without resizing the opening 518. Light emitted from the optical metrology device 582 travels through the openings 584, 586, and 518 toward the substrate support 504. The light reflects from a substrate disposed on the substrate support 504 and travels back through the openings 518, 586, and 584 to the optical metrology device 582. Further details of the optical metrology device 582 are described below in connection with FIGS. 9A-10C. A recess in the gas cap 564 accommodates an upper portion of the optical metrology device 582 that protrudes above the second zoned plate 558.

Figure 5B:
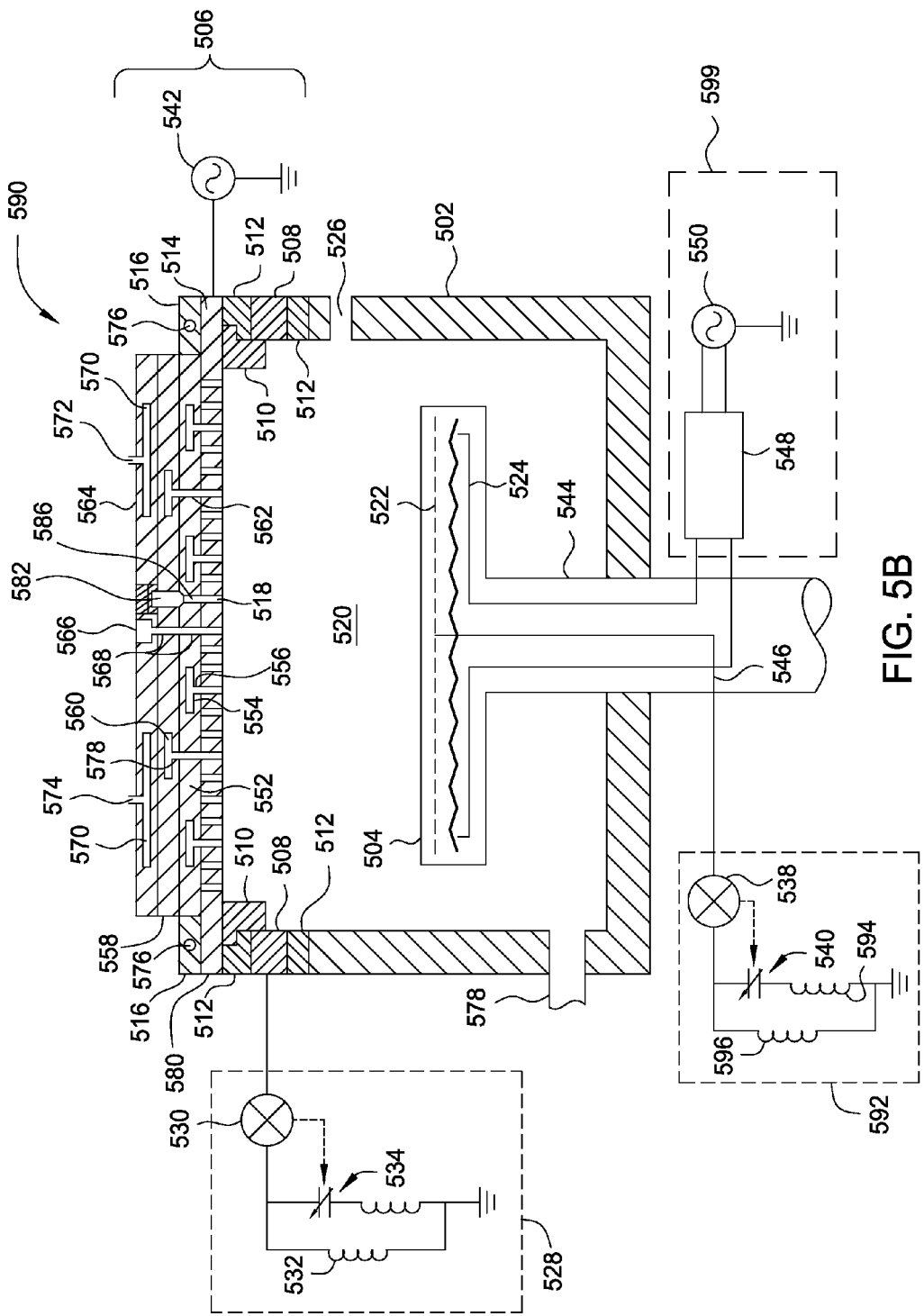
FIG. 5B is a schematic cross-sectional view of an apparatus according to another embodiment.

FIG. 5B is a schematic cross-sectional view of a processing chamber 590 according to another embodiment. The processing chamber 590 of FIG. 5B is similar in many respects to the processing chamber 500 of FIG. 5A, and identical elements are numbered the same in the two figures. The processing chamber 590 features a different tuning circuit 592 coupled to the substrate support 504. The tuning circuit 592 has the same components as the tuning circuit 528, namely the electronic controller 540, the electronic sensor 538, a first inductor 594 in series with the electronic controller 540, and a second inductor 596 in parallel with the electronic controller 540.

The tuning circuit 592 operates in a manner similar to the tuning circuit 536 of FIG. 5A. The tuning circuit 592 has a variable impedance, with a range set by the properties of the electronic components of the circuit, the electrode 522, and the plasma. At least one of the electronic components of the tuning circuit 592 is variable to provide a variable impedance that may be controlled. Varying the impedance of the tuning circuit 592 controls the density profile of the plasma in the processing volume 520.

Figure 6:
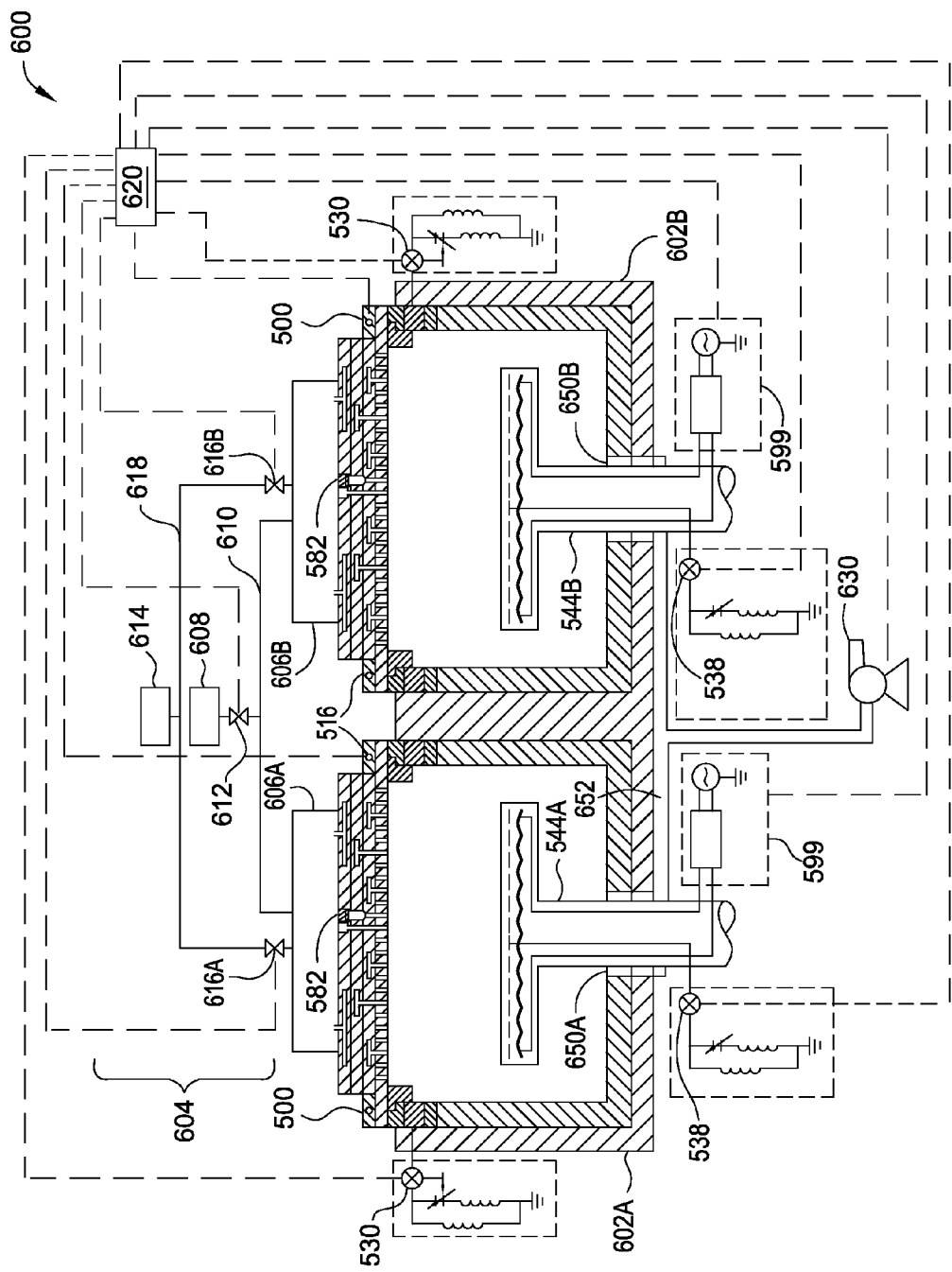
FIG. 6 is a schematic cross-sectional view of an apparatus according to another embodiment.

FIG. 6 is a schematic cross-sectional view of an apparatus 600 according to another embodiment. The apparatus 600 is a tandem unit of two process chambers 602A and 602B. Each of the process chambers 602A and 602B may be any of the chambers 300, 400, 500, and 590. Typically the chambers 602A and 602B are substantially identical, but they need not be. In FIG. 6, the process chambers 602A and 602B are identical, and are each similar to the chamber 590 of FIG. 5B. Each of the chambers 602A and 602B has a respective exit portal 650A and 650B disposed around their respective substrate support shafts 544A and 544B. The chambers 602A and 602B are evacuated through a common vacuum line 652 coupled to a common vacuum source 630. The apparatus 600 comprises a gas delivery system 604 that delivers process gases to respective gas manifolds 606A and 606B on the lids of the chambers 602A and 602B. The gas delivery system 604 comprises at least one gas source 608 coupled by a common flow control device 612 to the gas manifolds 606A and 606B by a common delivery conduit 610. The gas delivery system also comprises at least one gas source 614 coupled by individual flow control devices 616A and 616B to the gas manifolds through an individual delivery conduit 618. Separation of gas flows into commonly controlled flow and individually controlled flows allows for closer control of process gas flows to each chamber, if desired, while maintaining common flow control of ambient gases to each chamber.

A controller 620 is coupled to the various control features of the apparatus 600, including the individual control devices 614, the common control device 612, the heater 516 of each chamber, the electronic sensors 530 and 538 of the tuning circuits that control the impedance of the respective tuning circuits, the optical metrology devices 582 of each chamber, and the bias generation circuits 599 for each chamber. The controller 620 monitors progression of the deposition using the optical metrology devices 582 and adjusts gas flows, plasma density profiles, and temperature of each of the conductive gas distributors to achieve a desired uniformity for each deposition.

Figure 7:
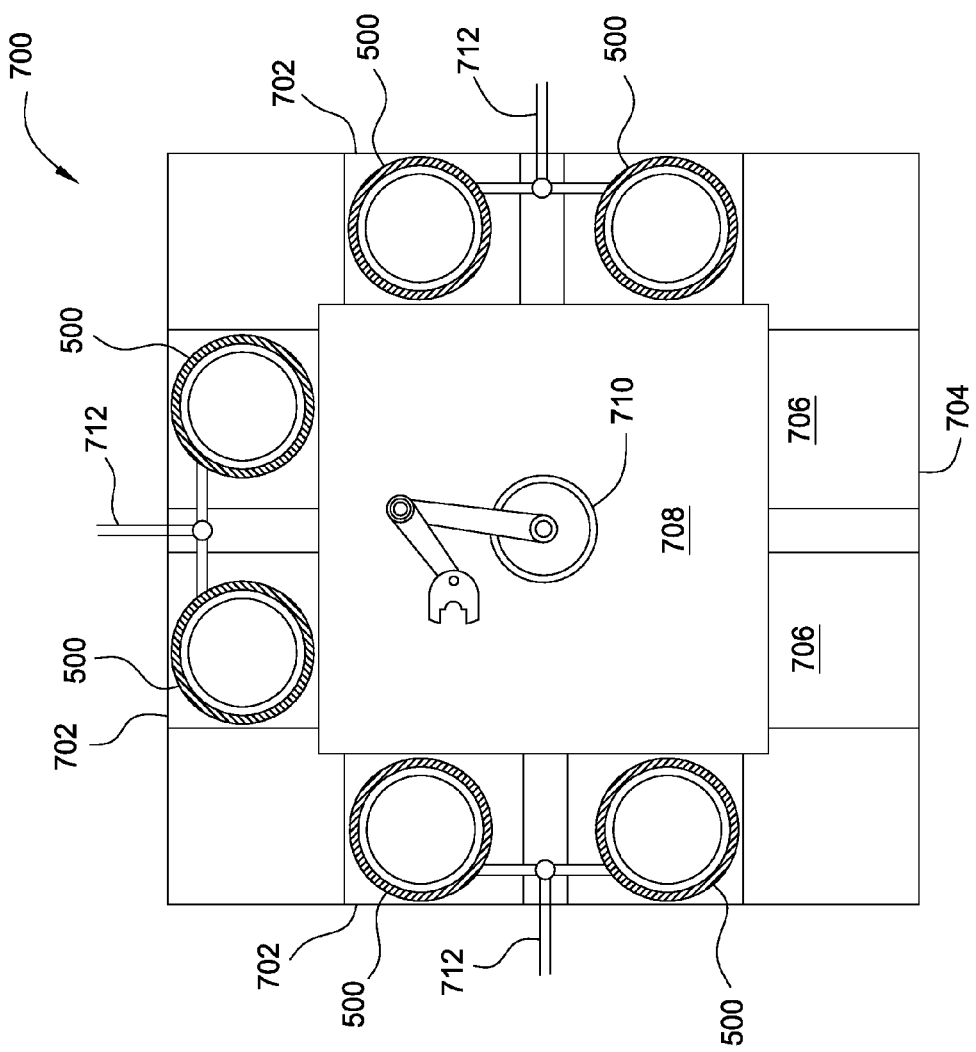
FIG. 7 is a schematic top view of an apparatus according to another embodiment.

FIG. 7 is a schematic top view of an apparatus 700 according to another embodiment. The apparatus 700 is a collection of processing chambers, all of which may be embodiments of the processing chamber 500 of FIG. 5A, coupled to a transfer chamber 708 and a load-lock assembly 704. The processing chambers 590 of FIG. 5B, 300 of FIG. 3, and 400 of FIG. 4 may also be used. The processing chambers 500 are generally grouped in tandem units 702, such as the tandem unit 600 of FIG. 6, each of which has a single supply of process gases 712. As noted in the description accompanying FIG. 6, flow of process gases may be commonly controlled to the two chambers of the tandem unit 600 in the apparatus 700, and/or individually controlled to each chamber of the tandem unit 600. The tandem units 702 are positioned around the transfer chamber 708, which typically has a robot 710 for manipulating substrates. The load-lock assembly 704 may feature two load-lock chambers 706, also in a tandem arrangement. The apparatus 700 is generally suited to practicing methods described herein in a production environment with high throughput. It should be noted that any of the chamber embodiments described herein, the apparatus 300, 400, 500, or 590, may be used in the apparatus 700 in any combination.

Figure 8A:
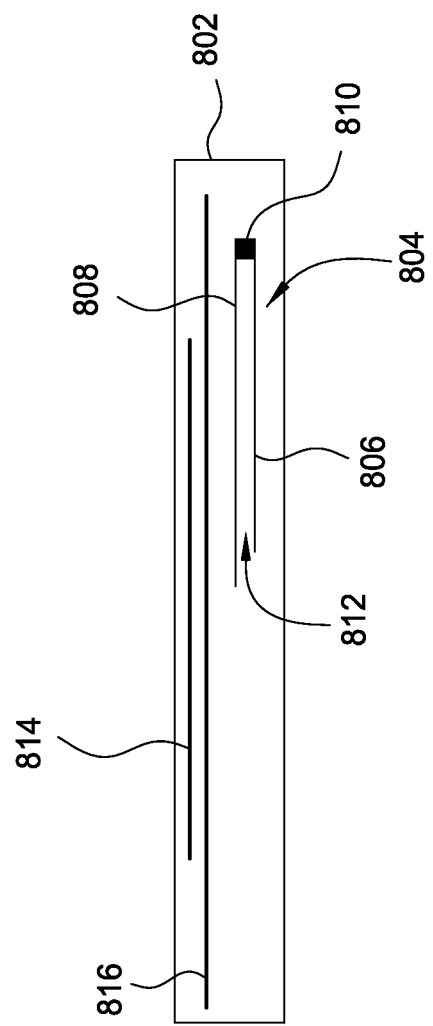
FIG. 8A is a schematic section view of a substrate support with a multi-zone heater that may be used with the other apparatus and methods disclosed herein.

FIG. 8A is a schematic section view of a substrate support 802 with a multi-zone heater that may be used with the other apparatus and methods disclosed herein to control a temperature profile of a substrate disposed on the substrate support 802. The substrate support 802 has an embedded thermocouple 804. An embodiment of the substrate support 802 may be made using a hot press sintering process in which AlN in powder form may be pressed into a mold and heated. In an exemplary embodiment, the substrate support 802 may be formed by layering AlN powder into the mold to form a first layer of AlN, positioning a first heating element 814, which may be a resistive heating element, over the first layer of AlN, depositing a second layer of AlN power over the first heating element 814, positioning a second heating element 816 on the second layer of AlN powder, adding a third layer of AlN power over the second heating element 816, positioning the thermocouple 804 on the third layer of AlN, and then depositing a fourth layer of AlN powder over the thermocouple 804. Note that this procedure forms the substrate support 802 in an inverted position relative to that shown in FIG. 8A.

If the electrodes described above are to be included, the layering process as described above may be extended to provide for a bias electrode and a tuning electrode either before the heating elements 814 and 816, and the thermocouple 804, or after. Once the layers of AlN powder, the heating elements 814 and 816, the thermocouple 804, and any desired electrodes are in place, high pressure and high temperature (as are known in the art) may be applied to the structure to include sintering. The result is the formation of a solid substrate support 802 as shown in FIG. 8A. Note that the above example described steps for forming a two zone substrate support. In other embodiments, 3, 4, 5, and 6 or more zone substrate supports may be made with appropriate corresponding layering steps and additional heating elements and thermocouples.

In some embodiments, the thermocouple 804 may include a longitudinal piece of a first material 806 and a longitudinal piece of a second material 808. The first material and the second material typically have a melting point high enough to avoid damage during the manufacturing process described above, a difference in Seebeck coefficients sufficient to generate a voltage signal corresponding to small temperature variations, and a coefficient of thermal expansion close to that of the substrate support material so that neither the thermocouple 804 nor the substrate support 802 is damaged by thermal stresses during temperature cycles.

The first material 806 and the second material 808 may be shaped in bars, wires, strips, or any other practicable shape that can both extend radially from the center of the substrate support 802 to an outer heating zone of the substrate support 802 and also have sufficient surface area at both ends to allow formation of reliable electrical connections. At the junction end 810 of the longitudinal pieces 806 and 808, the longitudinal pieces 806 and 808 may be welded together and/or otherwise connected using a conductive filler material.

In embodiments where the thermocouple junction 810 is formed by welding, a welding method should be chosen that allows the junction 810 to remain intact and tolerate heat applied during the sintering process. For example, tungsten inert gas (TIG) welding or similar techniques may be used to weld a piece of W5Re, W26Re or other conductive materials to the W5Re and W26Re longitudinal pieces 806 and 808 to form welded junctions that will not melt during sintering.

Thus, in some embodiments, a method of forming the thermocoupled junction 810 is to sandwich a filler material between W5Re and W26Re strips that function as the longitudinal pieces 806 and 808. The filler material may be a metal with resistivity not higher than either W5Re or W26Re and have a melting point above sintering temperatures. Examples of suitable filler materials for use with W5Re and W26Re strips used as the longitudinal pieces 806 and 808 include W5Re, W26Re, tungsten (W), molybdenum (Mo), and similar materials. In some embodiments, the hot press sintering process could be used to bond the filler material to the W5Re and W26Re longitudinal pieces 806 and 808.

An insulating material may be inserted in the space 812 between the longitudinal pieces 806 and 808 or the AlN powder may be forced into the space 812 between the pieces 806 and 808. If AlN is used to insulate the thermocouple pieces 806 and 808 from each other, a thickness of at least 0.5 mm of AlN is usually sufficient. Additional thickness may be used. Note that although the longitudinal pieces 806 and 808 shown in FIG. 7 are disposed one over the other, in other embodiment, the longitudinal pieces 806 and 808 may be spaced lateral to each other, and thus may be disposed at the same vertical position within the substrate support 802. Such an arrangement may facilitate depositing insulating AlN powder into the space 812 between the pieces 806 and 808 during manufacturing.

Figure 8B:
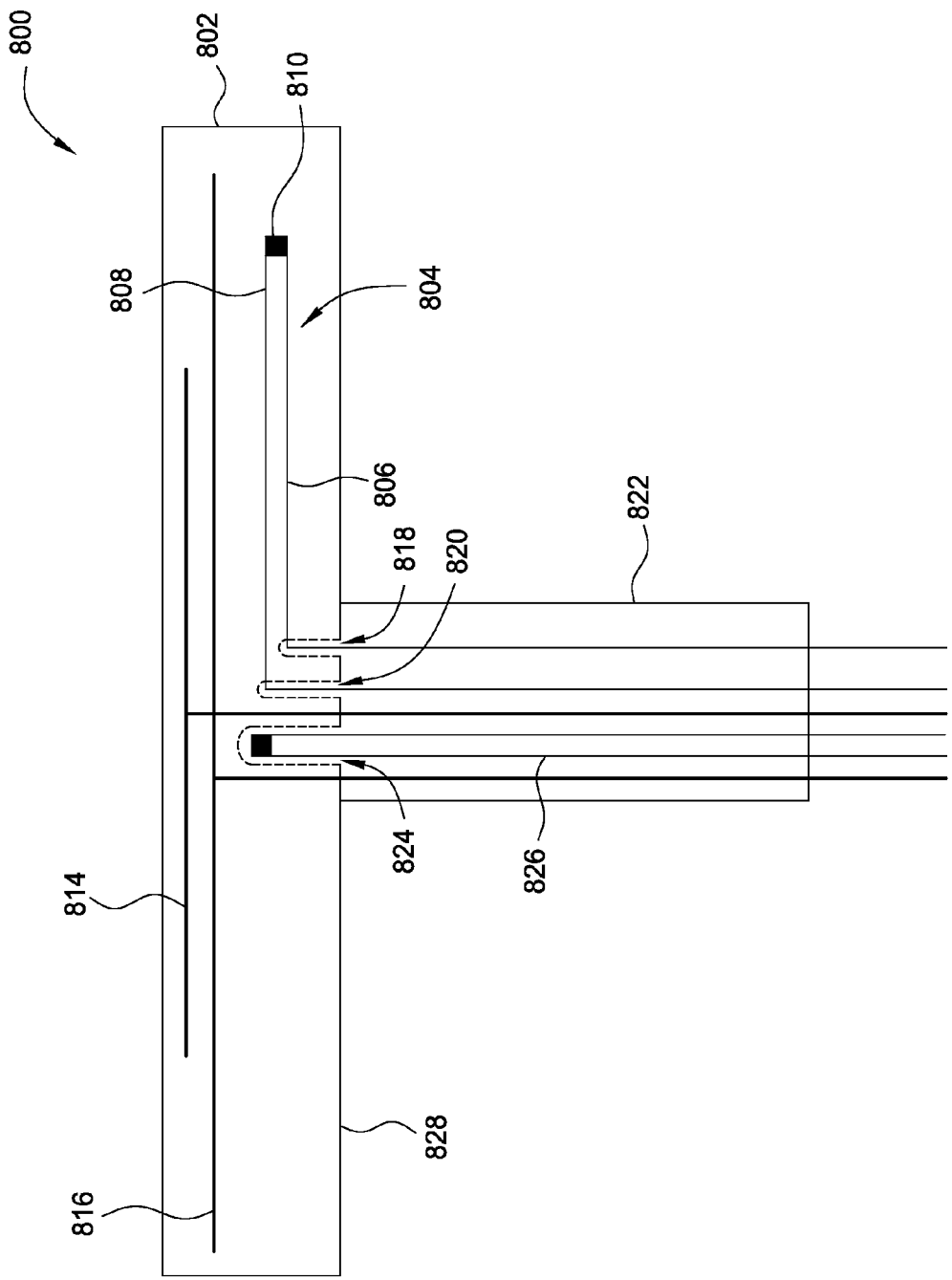
FIG. 8B is a schematic section view of a substrate support having additional features.

FIG. 8B is a schematic section view of a multi-zone substrate support 800 having additional features. After sintering the substrate support 802 of FIG. 8A, holes 818 and 820 are opened in the center of the lower surface 824 of the substrate support 802. Holes 818 and 820 extend to expose the longitudinal pieces 806 and 808. Any practicable method (e.g., drilling) of opening a hole in the substrate support 802 may be used. The holes 818 and 820 are made of sufficient diameter to allow connectors (e.g., conductive wires) to be connected to the longitudinal pieces 806 and 808. In some embodiments, the same materials used for the longitudinal pieces 806 and 808 may be used for the connectors, respectively. In some embodiments, the connectors are a different material than the longitudinal pieces 806 and 808. In such cases, the measured temperature will be based on the temperature different between the thermocoupled junction 810 location and the connector connection points in the center of the substrate support 802. For a dual-zone support, the connector connection points are proximate to a conventional thermocouple 826 used to measure the temperature of the inner zone and which is disposed at the center of the substrate support 802. Assuming the temperature of the connection connection points is the same as the temperature of the inner zone, the temperature at the thermocouple junction 810 location can be calculated.

In some embodiments, the connectors are brazed, welded, or soldered to the longitudinal pieces 806 and 808. The brazing process may be performed in an oxygen free environment to avoid oxidation of the materials. In addition, a hole 824 may be opened to insert the conventional thermocoupled 826 into the substrate support 802 for the inner heating zone. Note that although not shown, additional holes for connectors to the heating elements 814 and 816 may also be opened and the connections to the elements 814 and 816 made.

The shaft 822 may next be attached to the center of the lower surface 828 of the substrate support 802. In some embodiments, the shaft 822, which houses the connectors to the longitudinal pieces 806 and 808, a connector to the conventional thermocouple 826, and connectors to the heating elements 814 and 816, may be attached to the substrate support 802 before the various connectors are attached to the respective thermocouples 826 and 804, and the heating elements 814 and 816.

FIG. 8C shows the multi-zone substrate support 800 of FIG. 8B disposed in a processing chamber, such as the processing chamber 502. The connectors from the thermocouples 826 and 804, and the heating elements 814 and 816, are coupled to a controller 832 that may include a processor and appropriate circuitry adapted to both receive and record signals from the thermocouples 826 and 804, and apply current to the heating elements 814 and 816. The multi-zone support 800 of FIG. 8B may be disposed in any of the chambers 300, 400, 500, and/or 590, and as mentioned above, may also include bias electrodes and tuning electrodes.

Figure 9A:
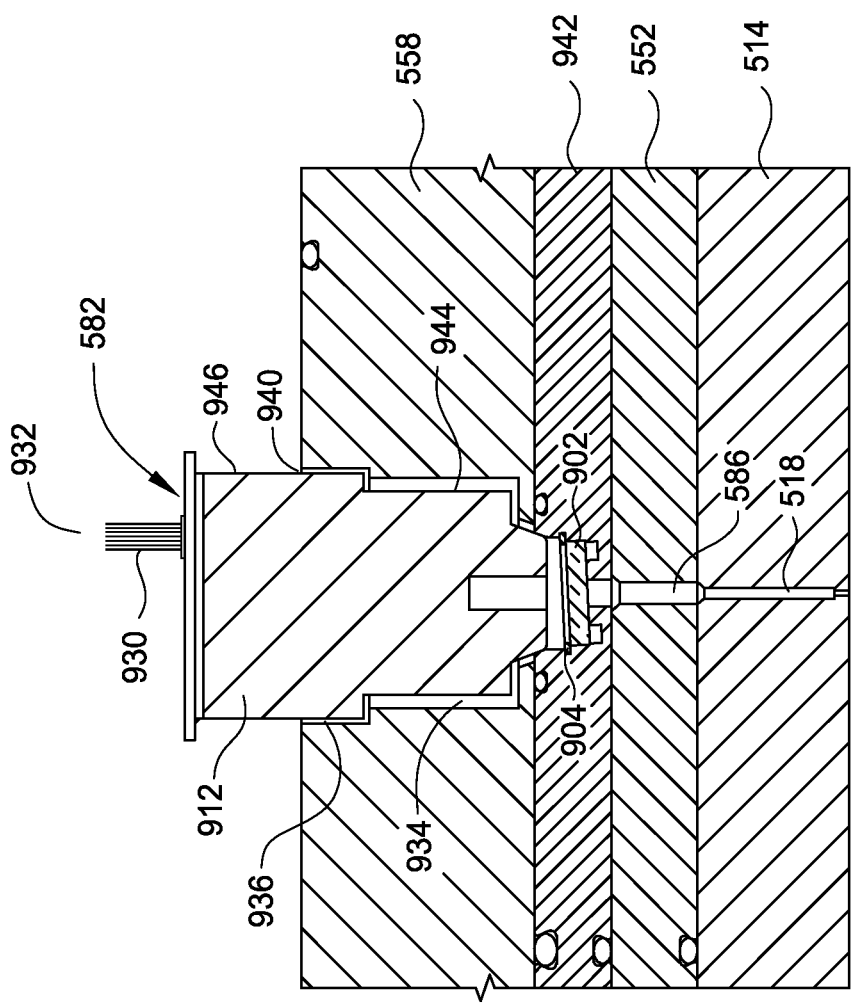
FIG. 9A is a schematic cross-sectional illustration of a chamber lid assembly with an optical metrology device according to one embodiment.
Figure 9B:
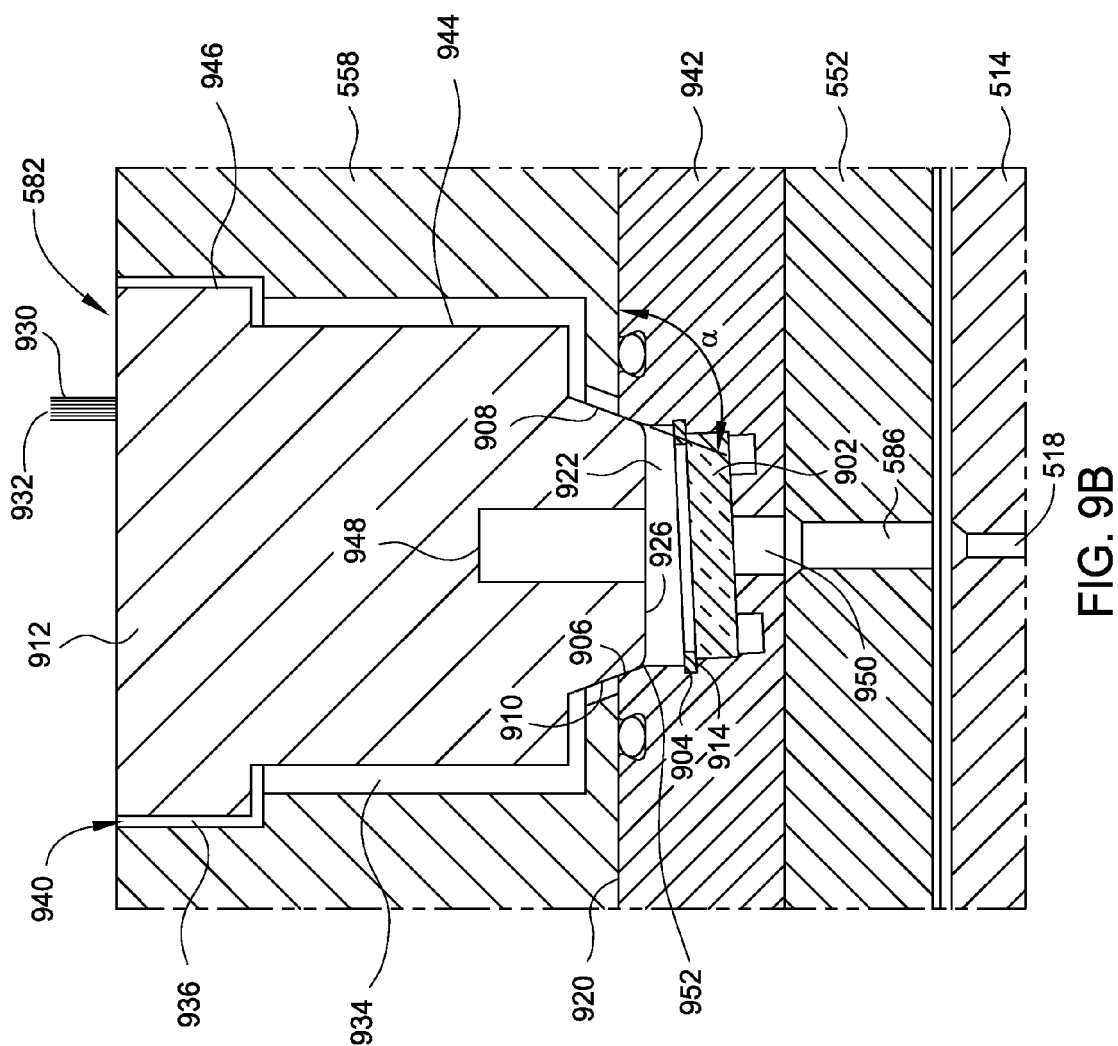
FIG. 9B is a more detailed view of the optical metrology device of FIG. 9A.

FIG. 9A is a schematic cross-sectional illustration through the center of the optical metrology device 582 according to one embodiment. FIG. 9B is a close-up cross-sectional view through the center of the optical metrology device 582 of FIG. 9A. As shown, the metrology device 582 includes a collimator 912 that rests within an opening 940 in the second zoned plate 558. In the embodiment of FIG. 9A, the metrology device 582 extends into an optional seating plate 942, disposed between the first zoned plate 552 and the second zoned plate 558. The seating plate 942 may also be a zoned plate, or the seating plate 942 may merely pass gas flows between the first zoned plate 552 and the second zoned plate 558. The first zoned plate 552 has a window 902 disposed therein for preventing flow of process gases into the collimator 912, which might damage optical elements inside the collimator 912. The window 902 may be any material capable of admitting light from the collimator 912 through the first zoned plate 552, such as sapphire, quartz, or glass of any appropriate composition.

The opening 940 and the collimator 912 together define a first gap 934 and a second gap 936. The first gap 934 surrounds a first portion 944 of the collimator 912, and the second gap 936 surrounds a second portion 946 of the collimator 912. The first portion 944 of the collimator 912 may have a cylindrical shape, while the second portion 946 may have a box shape. The first gap 934 may be larger than the second gap 936 to accommodate a tilting or rotating motion of the collimator 912, as described in more detail below.

The window 902 is held on a ledge 914 within the seating plate 942 by a window holder 904. The window 902 is disposed at an angle relative to the substrate during processing. During operation, a light, which is typically a broad spectrum light, such as light from a xenon lamp, is provided from a light source (not shown) to the collimator 912 through a fiber bundle (not shown). The light passes through the collimator 912, which contains optics that align the light with the openings 586 and 518 and compress the light to a diameter substantially within the diameter of the openings 586 and 518. The light then passes through the window 902, through an opening 950 formed in the seating plate 942, through the opening 586, and through the opening 518 formed through the conductive gas distributor 514, illuminating the substrate. The light is then reflected back from the substrate through the openings 518, 586, and 950 to the collimator 912. The window 902 is disposed at an angle to prevent direct reflection of outbound light from the collimator 912 back into the collimator 912. Angling the window 902 is optional, so the angle may be any angle between about 0° to about 25°, such as between about 1° and about 10°, for example about 3°. Reflected light from the substrate is passed from the collimator out through a fiber bundle (not shown) to a spectrometer or other spectral light analyzer (such as a photodiode, a photodiode array, or a CCD array).

Using the above described structure, metrology may be performed during substrate processing. Gas may be flowing through the openings 518 and the substrate may be processed while the light from the collimator 912 (and reflected from the substrate) passes through the openings 518. The openings 518 are sized for gas flow uniformity through the conductive gas distributor 514, and are thus typically similar in dimension to openings 518 of the conductive gas distributor 514 that are not used for in situ metrology. In one embodiment, the opening 518 has a diameter of 0.0028".

Light enters the collimator 912 through a conduit 930 with a plurality of optical fibers 932 forming an optical fiber bundle. The collimator 912 features optics (not shown), such as lenses and mirrors, that redirect light from the optical fiber bundle 932 to an opening 948 in the collimator 912. The optics align the light emerging from the collimator 912 through the opening 948 with the openings 950, 586, and 518, and focus or shape the light to fit through the smallest dimension of the openings 950, 586, and 518. The light is directed along a path that is perpendicular to a plane formed by two diameters of the substrate, so that the light is substantially perpendicular to the substrate surface. The optics also shape the light such that light reflected from the substrate surface also passes substantially through the openings 518, 586, and 950 into the collimator 912 for passage out through the fiber bundle 932 to the spectral light analyzer.

During processing, various chamber components, such as the first zoned plate 552, the second zoned plate 558, the conductive gas distributor 514, and the optional seating plate 942, may experience thermal expansion and contraction. Thus, the collimator 912 could be easily misaligned with the openings 586 and 518 unless properly disposed within the chamber. To ensure proper alignment of the collimator 912 with respect to the openings 586 and 518, the collimator 912 has a tapered extension 926 with a slanted sidewall 908, for example a frustroconical extension, that engages a recess 922, which may be a tapered bore, with a correspondingly slanted wall 906 formed in the seating plate 942. In an embodiment without the optional seating plate 942, the recess may be formed in the first zoned plate 552. The second zoned plate 558 may also have a slanted wall 910 to accommodate the extension 926. The walls 908, 910 and tapered extension 926 may be angled at an angle "a" relative to a top surface 920 of the seating plate 942. The collimator 912 extends into the recess 922 of the seating plate 942 and thus, when the seating plate 942 moves laterally due to thermal expansion/contraction, the collimator 912 correspondingly moves and thus remains properly aligned with the openings 586 and 518. The angle "a" may be any angle that results in effective transmission of a lateral force of thermal expansion in the seating plate 942 to the extension 926 of the collimator 912 without generating an axial force that unseats the collimator 912 from the recess 922. Typically, the angle "a" is between about 100° and about 145°, such as 120°.

The conductive gas distributor 514 and first zoned plate 552 are typically exposed to higher temperatures than the second zoned plate. In a typical operation, the conductive gas distributor 514 may heat to temperatures between about 300° C. and about 600° C., while the second zoned plate 558 may see temperatures 50° C. to 100° C. less than the conductive gas distributor 514. In an embodiment where the first zoned plate 552 and the conductive gas distributor 514 are aluminum, the differential expansion between the first zoned plate 552 and the conductive gas distributor 514 may be 10 nm to 100 nm, and the differential expansion between the conductive gas distributor 514 and the second zoned plate 558 may be 200 nm to 500 nm, resulting in a slight variation of alignment between the collimator 912 and the opening 940.

The first opening 934 and the second opening 936 are sized such that the collimator 912 may move laterally, as the seating plate 942 moves, without touching the second zoned plate 558. In a typical embodiment, the collimator 912 may move laterally by a distance up to about 0.03 inches, for example about 0.02 inches, as thermal cycles cause expansion and contraction of the seating plate 942. The first and second gaps 934 and 936 are typically sized to accommodate this motion without contact between the collimator 912 and the second zoned plate 558. The first gap 934 may have a dimension of up to about 0.15 inches, such as between about 0.04 inches and about 0.12 inches, for example about 0.10 inches. The second gap 936 may have a dimension that is in the same range as the first gap 934, up to about 0.15 inches, such as between about 0.04 inches and about 0.12 inches. The second gap 936 may be smaller or larger than the first gap 934. In the embodiment of FIGS. 9A and 9B, the second gap 936 is smaller than the first gap 934, having an exemplary dimension of about 0.08 inches.

The tapered extension 926 of the collimator 912 has an edge 952 that registers with the recess 922. The edge 952 is typically rounded or chamfered to reduce the opportunity for particle generation as the collimator 912 moves with the recess 922. The rounded edges 952 provide a slip surface between the collimator 912 and the walls 908 and 910 that reduces particle formation due to frictional forces at the interfaces. The radius of curvature of the rounded edges is typically less than 0.1", such as between about 0.05" and about 0.09", for example about 0.07".

Arranged in this way, the optical metrology device 582 of FIGS. 9A and 9B can perform an in-situ optical analysis of a substrate during processing. Light from the collimator passes through the opening 518 while process gases flow through the opening 518 into the chamber. The opening 518 through which the process gases flow may be sized to optimize uniformity of gas flow through the showerhead, with no consideration given to a size needed for metrology, and the metrology device can be fitted to the resulting opening size so that gas flow uniformity is not disturbed.

Figure 10A:
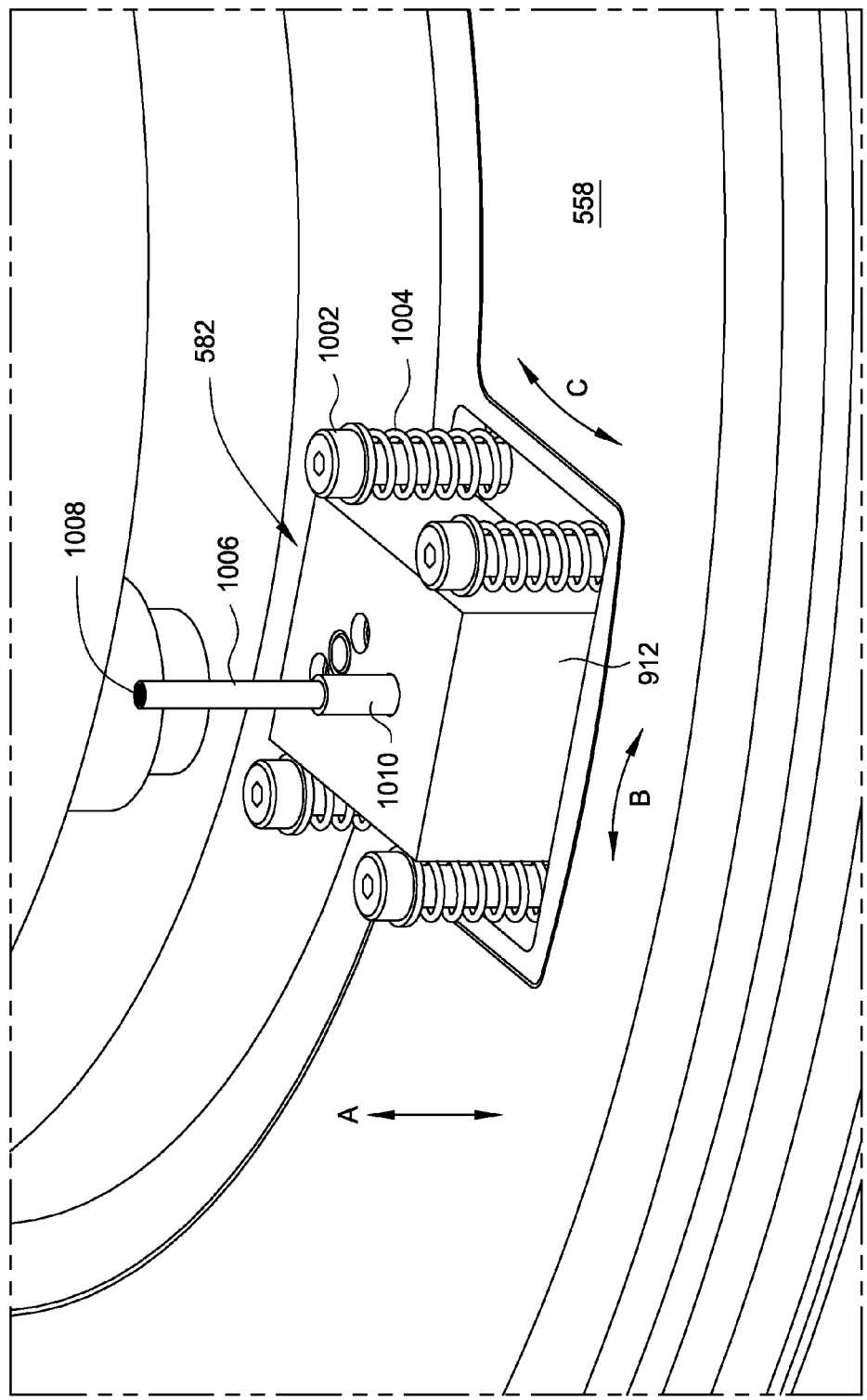
FIG. 10A is a schematic isometric illustrations of a lid assembly with a collimator according to one embodiment.
Figure 10B:
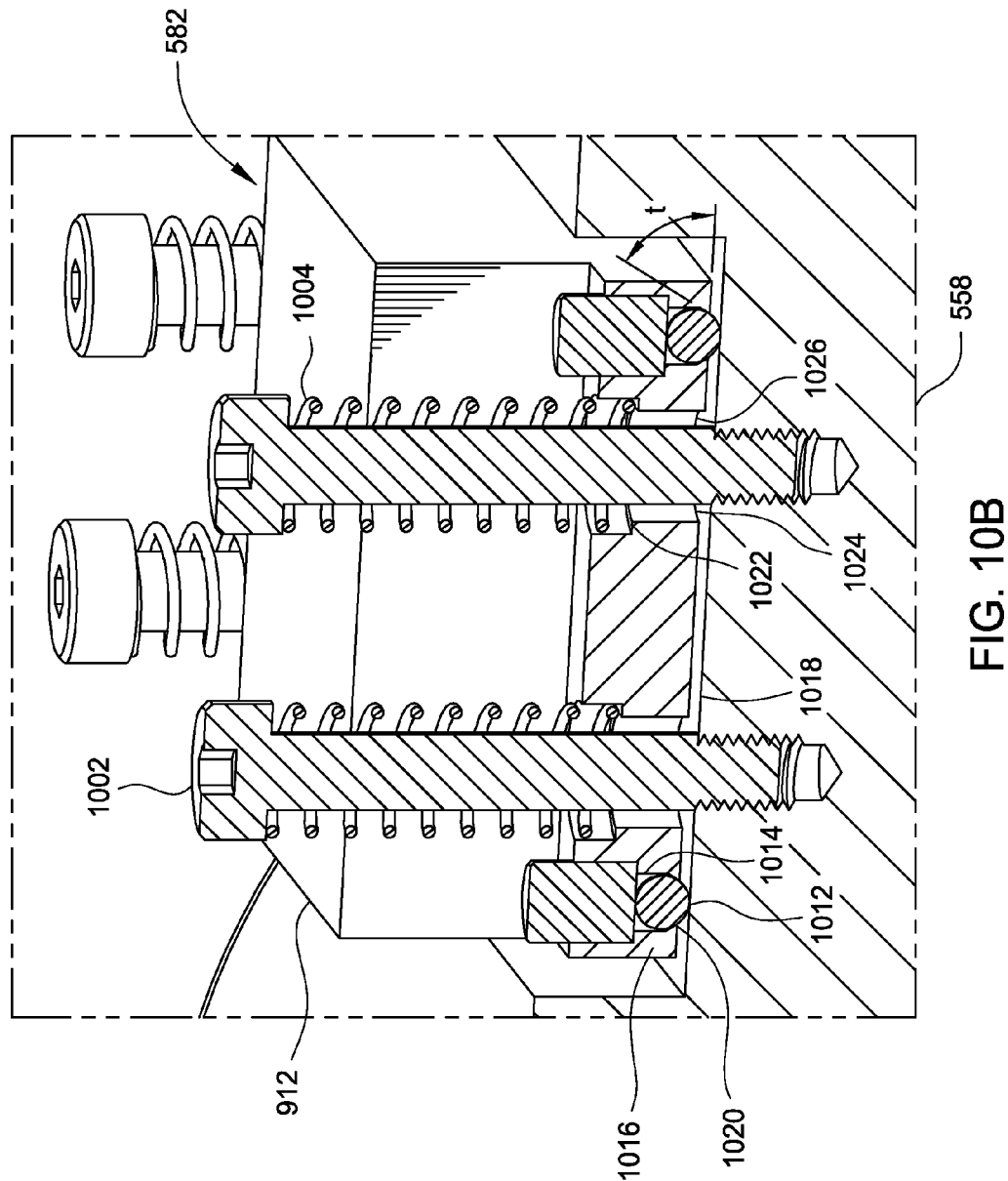
FIG. 10B is a cross-sectional view of a collimator according to one embodiment.
Figure 10C:
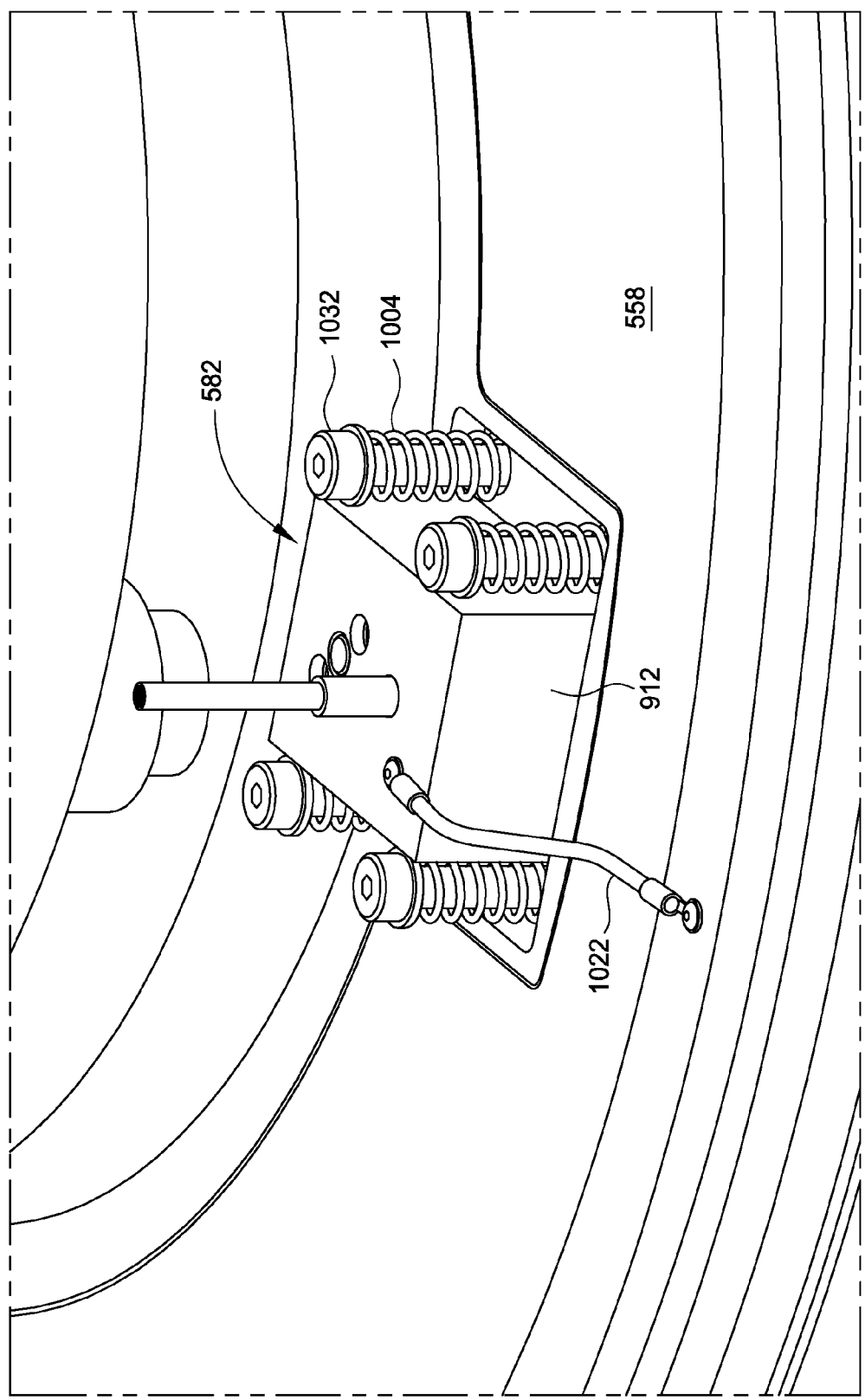
FIG. 10C is a schematic isometric illustrations of a lid assembly with a collimator according to another embodiment.

FIGS. 10A and 10C are schematic isometric illustrations of the mechanism used to mount the collimator 912 to the second zoned plate 558. FIG. 10B is a cross-sectional view of the collimator 912 through the mounting mechanism. As shown in FIG. 10A, four fasteners 1002, such as bolts, extend through the collimator 912 and are releasably secured to the second zoned plate 558. In one embodiment, the fasteners 1002 may comprise bolts. Resilient members 1004, which may be springs, are coupled between the head of each fastener 1002 and the collimator 912 such that the collimator 912 can remain attached to the second zoned plate 558, yet move in a direction shown by arrows "A" when thermal expansion causes the collimator 912 to move. The resilient members 1004 force the collimator 912 to remain seated in the recess 922 within the seating plate 942, so that lateral movement of the seating plate 942 under thermal stress causes lateral movement of the collimator 912. A conduit 1006 houses a bundle 1008 of optical fibers, and is coupled to the collimator 912 at a portal 1010. The optical fiber bundle 1008 carries light from a light generator (not shown) to the collimator 912 for projecting onto the substrate, and returns light reflected from the substrate through the collimator 912 to a light analyzer (not shown).

FIG. 3B shows a perspective cross-section of the collimator 912 drawn through the fastener 1002 on one side of the collimator 912. The cross-section of FIG. 10B is parallel to the cross-section of FIGS. 9A and 9B, but is viewed in perspective. The fasteners 1002 seat in the second zoned plate 558, and the resilient members 1004 contact the collimator 912 at a ledge 1022 to provide an axial force on the collimator 912, tending to keep the collimator seated. The fasteners 1002 pass through openings 1024 in the collimator 912. A gap 1026 between each fastener 1002 and its respective opening 1024 allows the collimator 912 to move laterally with respect to the fastener 1002 and with respect to the second zoned plate 558. The gap 1026 is sized to accommodate the lateral movement without contact between the collimator 912 and the fasteners 1002, and typically has a dimension up to about 0.15 inches, such as between about 0.04 inches and about 0.12 inches, for example about 0.10 inches.

Ball bearings 1012 are provided, each ball bearing 1012 seated in a socket 1014 formed in the collimator 912 at a surface 1016 that interfaces with a receiving surface 1018 of the second zoned plate 558. Each ball bearing 1012 rotates within its respective socket 1014 to allow the collimator 912 to move laterally while minimizing friction between the collimator and the second zoned plate 558. The sockets 1014 have side walls with a tapered portion 1020 that tapers toward the ball bearing 1012, forming an angle "n" with the surface 1016 to retain the ball bearing 1012 within the socket 1014 while allowing smooth rotation of the ball bearing. The angle "n" may be between about 40° and about 80°, such as between about 50° and about 70°, for example about 60°.

During operation, the first zoned plate 552, the seating plate 942, the conductive gas distributor 514 and the second zoned plate 558 are all electrically biased with RF power to substantially the same electric potential. Thus, an RF strap 1022 is used to electrically connect the collimator 912 to the second zoned plate 558 to ensure the collimator 912 remains at a substantially identical electrical potential as the second zoned plate 558.

The in situ metrology embodiments described herein may be used to determine layer thickness by refractive effects that depend on layer thickness. Light from the in situ metrology device illuminates the substrate, penetrating the layers and reflecting differentially from the interfaces between the layers according to the Fresnel equations. The reflected light produces an interference pattern with incident light and with reflected light from other layers. The interference pattern is governed by the thickness and composition of the layers. As one layer grows, the interference pattern changes with the thickness of the growing layer in a predictable way, so that an end point may be detected. The final interference pattern resolved during growth of the layer becomes a signature pattern that is used during deposition of subsequent layers to observe the change in the pattern as the subsequent layers are formed.

By utilizing a slanted interface between the collimator and a blocker plate, the collimator may remain substantially aligned with a gas passage formed through a gas distributor even when the blocker plate thermally expands/contracts. The collimator, by being disposed within a blocker plate and annular base plate, directs light, and receives reflected light, through the gas passage, even when the gas passage is in use (i.e., processing/cleaning gases are flowing therethrough). Thus, the metrology may be performed without negatively impacting process uniformity. Providing a passage for metrology that does not provide for gas flow through the passage may lead to process non-uniformity, since the passage would be above a portion of the substrate, and the gas flow in the vicinity of the passage would be non-uniform due to the lack of gas flow through the passage.

Figure 11:
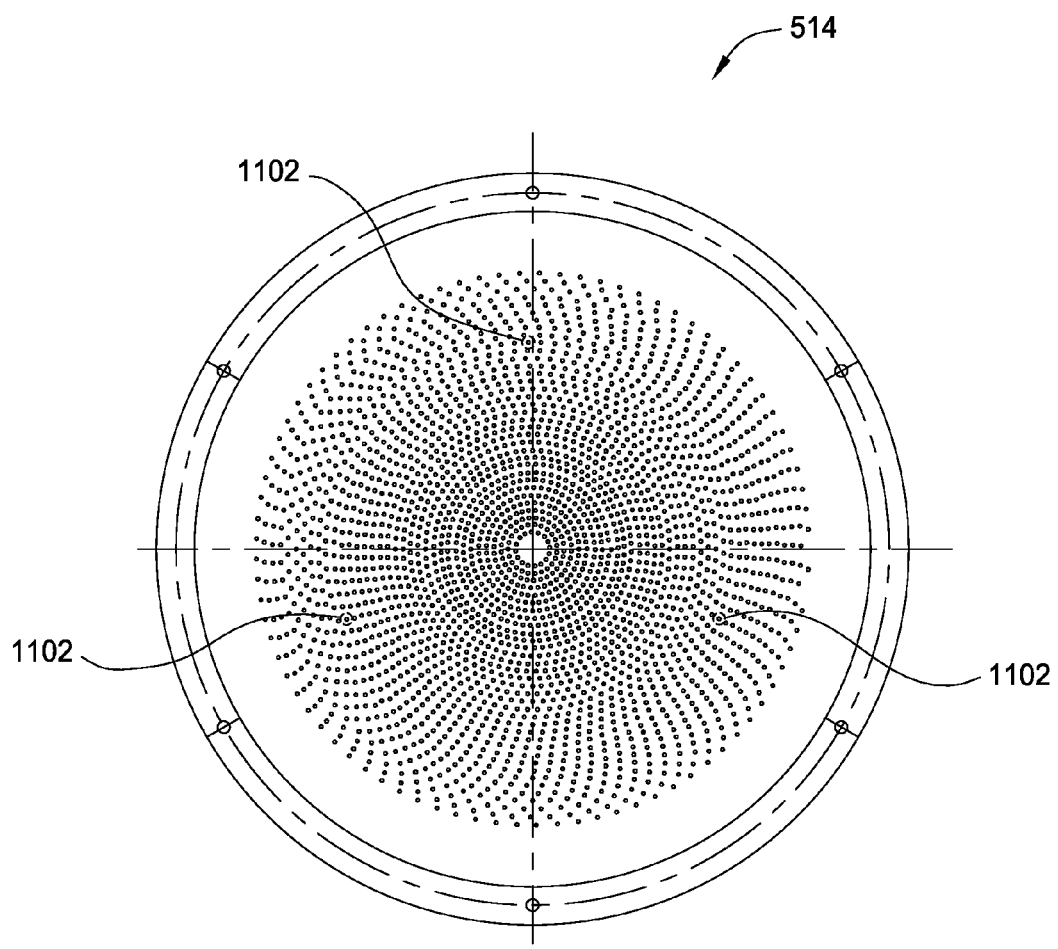
FIG. 11 is a bottom view of a conductive gas distributor using in-situ metrology according to one embodiment.

The embodiments described herein feature one in situ metrology device or configuration. It should be noted that some embodiments may feature multiple in situ metrology devices to monitor film formation at a plurality of locations on the substrate surface in real time. FIG. 11 is a bottom view of the conductive gas distributor 514 of FIGS. 5A and 5B illustrating use of in-situ metrology. Three openings 1102 are encircled in the embodiment of FIG. 11 indicating openings used for in-situ optical metrology, in addition to gas flow. The analysis locations may be distributed according to any desired pattern. In the embodiment of FIG. 11, three in situ metrology devices are provided in a distributed arrangement. The three in situ metrology devices may be positioned along a circle concentric with the substrate support, which is to say the three devices may be positioned to monitor three locations that are substantially the same distance from the center of a substrate positioned on the substrate support. Alternately, the three in situ metrology devices may be positioned at different distances from the center. Multiple monitoring devices may be useful to monitor deposition uniformity, both of thickness and composition, at different locations of the substrate surface, and to achieve closed-loop control of deposition rate and uniformity while depositing one layer or a plurality of layers in one chamber.

The optical metrology device described above in connection with FIGS. 9A-10C produces light that indicates the structure of layers on a substrate. Light of a known incident spectrum is directed normal to the substrate and reflects from the substrate surface. Some of the light penetrates through layers formed on the substrate and reflects from the layer interfaces, producing a reflected spectrum that is different from the incident spectrum. During deposition of a layer, the reflected spectrum changes as the thickness of the deposited layer changes. Comparing the reflected spectrum to the incident spectrum and to prior reflected spectra for the same layer enables accurate determination of the thickness of the deposited layer. Such measurements may be taken at multiple locations on the substrate to determine uniformity of layer thickness and enable corrective actions to control the uniformity. Such measurements may also be used to detect when the layer thickness has reached a target value so deposition can be discontinued.

Incident light reflecting from two surfaces of a layer that has a thickness comparable to the wavelength of the light will exhibit a phase shift relative to the incident light. That phase shift is related to the film thickness and produces a characteristic interference pattern between the incident light and the reflected light. The reflected light thus has a spectral intensity that depends on the thickness of the layer. If the optical properties of a subjacent layer or material are known, a single pulse or flash of light may be reflected from the top layer, and comparison of the reflected light with the incident light using the Fresnel equations determines the thickness of the top layer.

If the optical properties of the subjacent layer are not known, multiple flashes or pulses of light may be used during deposition of the top layer to determine how the reflectivity changes with thickness of the top layer. Deposition rate and time may be used to compute layer thickness at the time of each light pulse. The reflectivity typically changes as a sinusoidal function of layer thickness. A curve may be fit to the reflectivity data to compute the reflectivity of the subjacent layer. The same comparison may be performed at multiple wavelengths, if a broad spectrum light source and spectral light analyzer are used, to increase convergence around the optical properties of the subjacent layer. The reflectivity of the subjacent layer may be expressed as a function of the reflectivity of the top layer, and the optical properties of the subjacent layer may be computed using the Fresnel equations.

If the subjacent layer is patterned, light reflected from the subjacent layer may have polarized components that contribute to the total reflected intensity in a root-mean-square relationship. Each wavelength of light reflected from the substrate will have a reflected intensity independent of the other wavelengths, and each wavelength of reflected light will behave according to the optical properties of the top layer and the subjacent layer. Thus, spectral analysis of multiple reflected wavelengths may be performed, using the computed top layer thickness and known top layer optical properties to fit the polar components of the subjacent layer reflectivity, and the optical properties of the subjacent layer that give rise to those components.

Once the optical properties of the subjacent layer are determined, a complete model of the substrate reflectivity may be constructed, and the thickness of a deposited layer may be known from a single pulse of reflected light using the Fresnel equations. If multiple layers are deposited, reflectivity of each layer may be computed from the known optical properties of the layer being deposited, and the known optical properties of the subjacent layer, using a single pulse of light. Alternately, the optical properties of the subjacent layer may be reconstructed by analyzing multiple pulses as the deposition proceeds, as described above.

If the optical properties of the subjacent layer are known, thickness of the top layer may be computed from a set of reflectivity data $R(t,\lambda)$ by fitting a generalized sinusoid to the data, according to the following equation:

$$R(t, \lambda) = A(\lambda)\sin\left(2\pi \frac{t}{T(\lambda)} + \phi(\lambda)\right) + B(\lambda)$$

Layer thickness may then be computed from the phase shift parameter ($\lambda$), using the known relation between layer thickness and phase shift $$d = \lambda/4\pi n.$$

Alternately, the period $T(\lambda)$ may be used to compute deposition rate $$D_r = \lambda/2n(\lambda)T(\lambda).$$

The phase and period of the reflectivity data depend on wavelength, so multiple wavelengths of data may be used to converge on thickness and/or deposition rate.

The reflectivity of the layer being deposited may also be related to the reflectivity of the subjacent layer using a variation of the Fresnel equations, as follows:

$$R_j(\lambda, t) = \frac{r_j(1 - r_j R_{j-1}) + (R_{j-1} - R_j)e^{-i2\beta_j}}{1 - r_j R_{j-1} + r_j(R_{j-1} - r_j)e^{-i2\beta_j}}$$

where $R_j$ is the reflectivity of layer "j", $R_{j-1}$ is the reflectivity of layer "j−1", which is the subjacent layer, and the other parameters are defined, as follows:

$$r_j = \frac{1 - N_j}{1 + N_j}$$

$$\beta_j(\lambda) = \frac{2\pi N_j(\lambda) D_R t}{\lambda}$$

$$N_j(\lambda) = n_j(\lambda) - ik_j(\lambda)$$

Relating the reflectivity of the top layer and the subjacent layer in this way enables calculation of the subjacent layer optical properties from the observed top layer reflectivity, and the known optical properties and deposition rate of the top layer.

Following is a description of an exemplary implementation of this general approach using a computer based processing scheme.

1. Input Data:

Experimental reflectivity data $R(\lambda,t)$ consists of L number of wavelengths ($\lambda$) and M time points (t) representing the reflectivity of the L wavelengths from the substrate at the M time points.

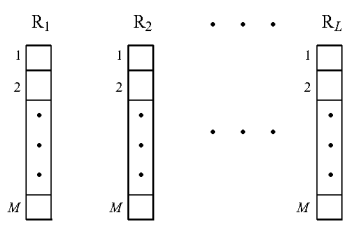

In a computer memory, the reflectivity R is stored sequentially as a one-dimensional array, according to:

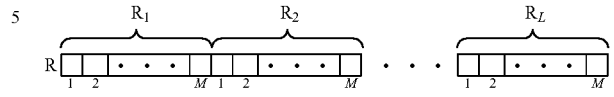

2. Modeling of Data:

The experimental data is fitted by a model, described by the following formulas derived from the Fresnel equations governing the reflective and refractive properties of light, including polarization to account for the polarizing effects of structures formed on the substrate:

$$f(\lambda, t) = w|F_1^s(\lambda, t)|^2 + (1-w)|F_1^p(\lambda, t)|^2 \quad (1)$$

$$F_1^s(\lambda, t) = \frac{r_1(1 - r_1 F_{sub}^s) + (F_{sub}^s - r_1)e^{-i2\beta_1}}{1 - r_1 F_{sub}^s + r_1(F_{sub}^s - r_1)e^{-i2\beta_1}} \quad (2)$$

$$F_1^p(\lambda, t) = \frac{r_1(1 - r_1 F_{sub}^p) + (F_{sub}^p - r_1)e^{-i2\beta_1}}{1 - r_1 F_{sub}^p + r_1(F_{sub}^p - r_1)e^{-i2\beta_1}} \quad (3)$$

$$\beta_1(\lambda, t) = \frac{2\pi(n_1 - ik_1)D_{R,1}t}{\lambda} \quad (4)$$

$$r_1(\lambda) = \frac{(1 - n_1) + ik_1}{(1 + n_1) - ik_1} \quad (5)$$

$$F_{sub}^s(\lambda) = A_{sub}^s(\lambda)e^{i\phi_{sub}^s(\lambda)} \quad (6)$$

$$F_{sub}^p(\lambda) = A_{sub}^p(\lambda)e^{i\phi_{sub}^p(\lambda)} \quad (7)$$

where w is a single constant (not a function of $\lambda$ or t), $n_1$ and $k_1$ are wavelength-dependent constants:

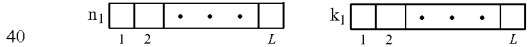

These formulas utilize the approach wherein reflectivity of the top layer and the subjacent layer are related, as described generally above.

3. Fit Parameters:

In the above equations, $D_{R,1}$ is a single variable (not a function of $\lambda$ or t), and $A_{sub}^s(\lambda)$, $\phi_{sub}^s(\lambda)$, $A_{sub}^p(\lambda)$, $\phi_{sub}^p(\lambda)$ are wavelength-dependent variables:

The above variables are fit parameters that may be adjusted to minimize the square of the difference between the experimental data $R(\lambda,t)$ and the model $f(\lambda,t)$, given by the following difference equation:

$$\chi^2 = \sum_{\lambda,t}^{L,M} |R(\lambda, t) - f(\lambda, t)|^2 \quad (8)$$

The total number of fit parameters (N) equals the number of wavelengths (L) multiplied by 4, plus 1 for $D_{R,1}$, i.e.:

$$N=(L\times 4)+1 \qquad (9)$$

4. Minimization Algorithm:

The minimization of $\chi^2$ utilizes an implementation of the iterative Levenberg-Marquardt (LM) algorithm to find the solution to the set of linear equations $$\sum_{k=1}^{N} A_{jk}\delta P_k = B_j \qquad (10)$$

$(A \cdot \delta P = B$ in matrix form), for the incremental values $\delta P_k$, that are added to the current approximation $P_k$ (k=1, 2, ..., N) of the fit parameter to give the next approximation. The elements $A_{jk}$ and $B_j$ are defined as:

$$A_{j,j} = \sum_{\lambda,t}^{L,M} \frac{\partial f(\lambda,t)}{\partial P_j}\frac{\partial f(\lambda,t)}{\partial P_j}(1+\Lambda) \qquad (11a)$$

$$A_{j,k} = \sum_{\lambda,t}^{L,M} \frac{\partial f(\lambda,t)}{\partial P_j}\frac{\partial f(\lambda,t)}{\partial P_k}(j\neq k) \qquad (11b)$$

$$B_j = \sum_{\lambda,t}^{L,M} (R(\lambda,t)-f(\lambda,t))\frac{\partial f(\lambda,t)}{\partial P_j} \qquad (12)$$

The partial derivative is approximated by the difference formula:

$$\frac{\partial f(\lambda,t)}{\partial P_j} = \frac{f(\lambda,t,P_j+h_j)-f(\lambda,t,P_j)}{h_j}, \qquad (13)$$

where $h_j$ is a pre-defined incremental value for each fit parameter $P_j$.

The LM algorithm can then be outlined as follows:
  a. Start with a set of initial guess values for the fit parameters P
  b. Calculate $\chi^2(P)$
  c. Choose a starting value for $\Lambda$, for example $\Lambda=0.001$
  d. Solve the linear equations (10) for $\delta P$, using Gauss-Jordan elimination algorithm
  e. Calculate $\chi^2(P+\delta P)$
  f. If $\chi^2(P+\delta P)\geq\chi^2(P)$, increase $\Lambda$ by a factor of 10 and go back to step d.
  g. If $\chi^2(P+\delta P)<\chi^2(P)$, decrease $\Lambda$ by a factor of 10, and update the fit parameters ($P=P+\delta P$)
  h. Repeat steps d to h until any one of the stop criteria is met:
    i. $\chi^2<\chi^2_{min}$
    ii. $\Delta\chi^2<\Delta\chi^2_{min}$
    iii. $L>L_{max}$
    iv. $L<L_{min}$ 5. Pseudo Code:

The following is a description of the above algorithm using a computer code-like language featuring generic function specifications found in most high-level computer programming languages.

```
TargetFunction(out A, out B, out χ²)
{
  Foreach p∈P, λ and t
  {
    Calc ∂f(λ, t)/∂p
  }
  χ² = 0
  ForEach λ and t
  {
    dy = R(λ, t) – f(λ, t)
    Foreach j∈P
    {
      wt = ∂f(λ, t)/∂Pj
      For(k = 0; k <= j; ++k)
      {
        A[j*P + k] += wt * ∂f(λ, t)/∂Pk
      }
      B[j] += dy*wt;
    }
    χ² += dy*dy*w;
  }
}
TargetFunction(A, B, pχ²)
Λ = 0.001
While (StopCriteria == false)
{
  Foreach pj∈P
  {
    A[i, i] *= (1.0 + Λ)
  }
  GaussJordan(A, B)
  Foreach pj∈P
  {
    pj = pj + bj
  }
  TargetFunction(A, B, nχ²)
  If(nχ² < pχ²)
  {
    Λ = Λ/10
  }
  Else
  {
    Λ = Λ*10
  }
}
```

6. Profiler Data:

A suitably configured computer programmed to perform the algorithm described above is expected to exhibit the distribution of CPU time in Table 1 when fitting the model to an experimental data set with 58 wavelengths.

TABLE 1

| # | Profiler data for 58 wavelengths | |
|---|---|---|
|   | Function | % CPU time |
| 1 | TargetFunction | 90 |
| 2 | GaussJordan | 8 |

7. Multi-Step Execution:

The algorithm described above may be performed repeatedly using subsets of data to efficiently converge upon an accurate fit of the model. In one example, an experimental data may consist of L=60 wavelengths. In such an example, the algorithm may be invoked multiple times, each with differing number of fit parameters, as follows:
  1. After a certain pre-defined time interval has passed (e.g. M=100), the first run involves only a limited number of wavelengths (e.g. L=15), so that the number of fit parameters N=15×4+1=61, including $D_{R,1}$.

2. The second step calculates the fit parameters $A_{sub}^s(\lambda)$, $\phi_{sub}^s(\lambda)$, $A_{sub}^p(\lambda)$, $\phi_{sub}^p(\lambda)$ for the remainder of the wavelengths not included in step 1. However, $D_{R,1}$ is fixed in this step, which means the fit parameters can be solved for each wavelength independently. The number of fit parameters N is 4, and the remainder 45 wavelength sets can be computed in parallel.
3. For experimental data in subsequent time-steps up to another pre-defined time interval (e.g. 100<M<200), there is only a single fit parameter $D_{R,2}$ ($\neq D_{R,1}$), and the computation proceeds one time-step at a time, solving for a new $D_{R,2}$ each time. This step also requires a new set of $n_2(\lambda)$ and $k_2(\lambda)$ constants, and new computations for $r_2(\lambda)$ and $\beta_2(\lambda,t)$.
4. Step 3 can be repeated multiple number of times sequentially, for new data in pre-defined blocks of time.

Figure 12:
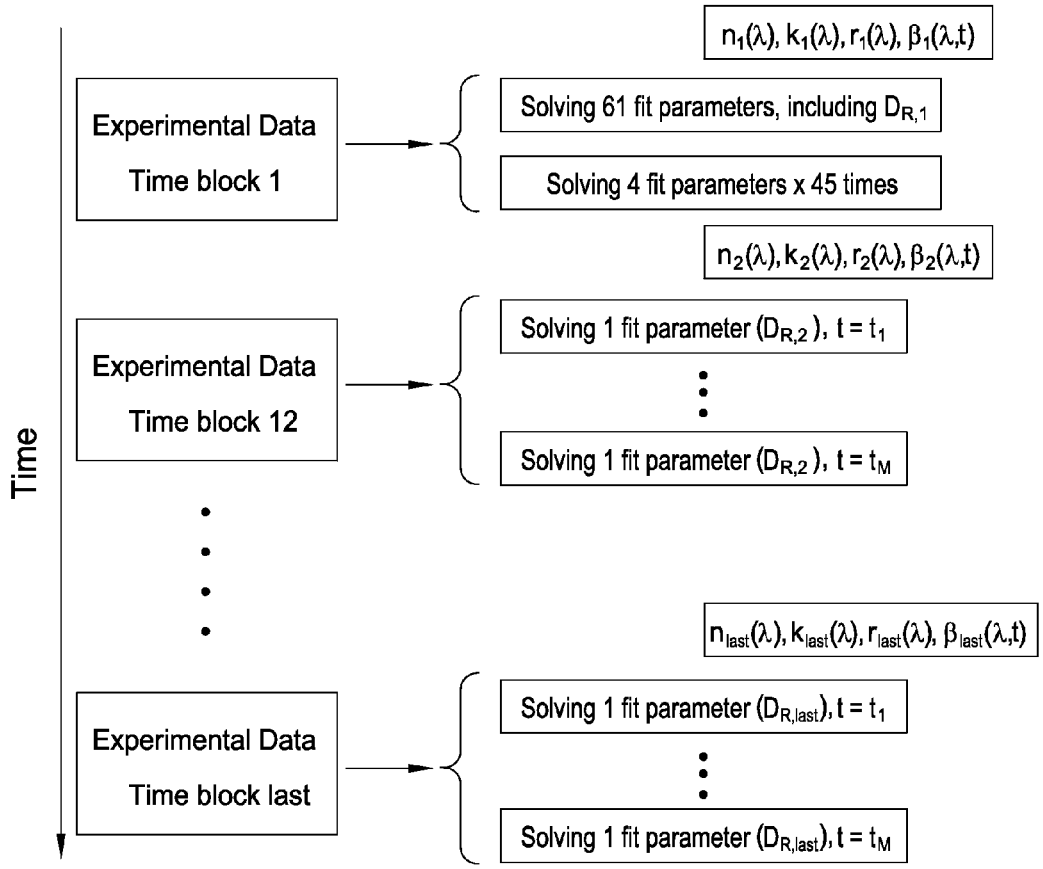
FIG. 12 is a flow diagram summarizing a method of determining layer thickness according to one embodiment.

The foregoing steps are summarized in the flow diagram of FIG. 12.

5. A second option of implementation runs the computation of step 1 above for data in multiple time intervals (blocks) simultaneously. However, it does not need to wait until all data are collected; the computation can begin after a certain pre-defined time interval has passed (e.g. M=100) within the first time block, and the fit parameters are continuously updated as new data arrive. Because of the change in $n(\lambda)$ and $k(\lambda)$ constants across time blocks, data in time blocks 2 and greater require a nested formulation of the model functions $f(\lambda,t)$, $F^s(\lambda,t)$ and $F^p(\lambda,t)$, fox example:

$$F_2^s(\lambda, t) = \frac{r_2(1 - r_2 F_1^s) + (F_1^s - r_2)e^{-i2\beta_2}}{1 - r_2 F_1^s + r_2(F_1^s - r_2)e^{-i2\beta_2}} \quad (14)$$

$$F_2^p(\lambda, t) = \frac{r_2(1 - r_2 F_1^p) + (F_1^p - r_2)e^{-i2\beta_2}}{1 - r_2 F_1^p + r_2(F_1^p - r_2)e^{-i2\beta_2}} \quad (15)$$

$$f(\lambda, t) = w(|F_1^s(\lambda, t_1)|^2 + |F_2^s(\lambda, t_2)|^2 + \ldots ) + \\ (1-w)(|F_1^p(\lambda, t_1)|^2 + |F_2^p(\lambda, t_2)|^2 + \ldots ). \quad (16)$$

The number of time blocks involved in this step may be pre-determined, for example 3.

6. After step 5 is completed, the calculation continues as in steps 2 to 4 above.

Figure 13:
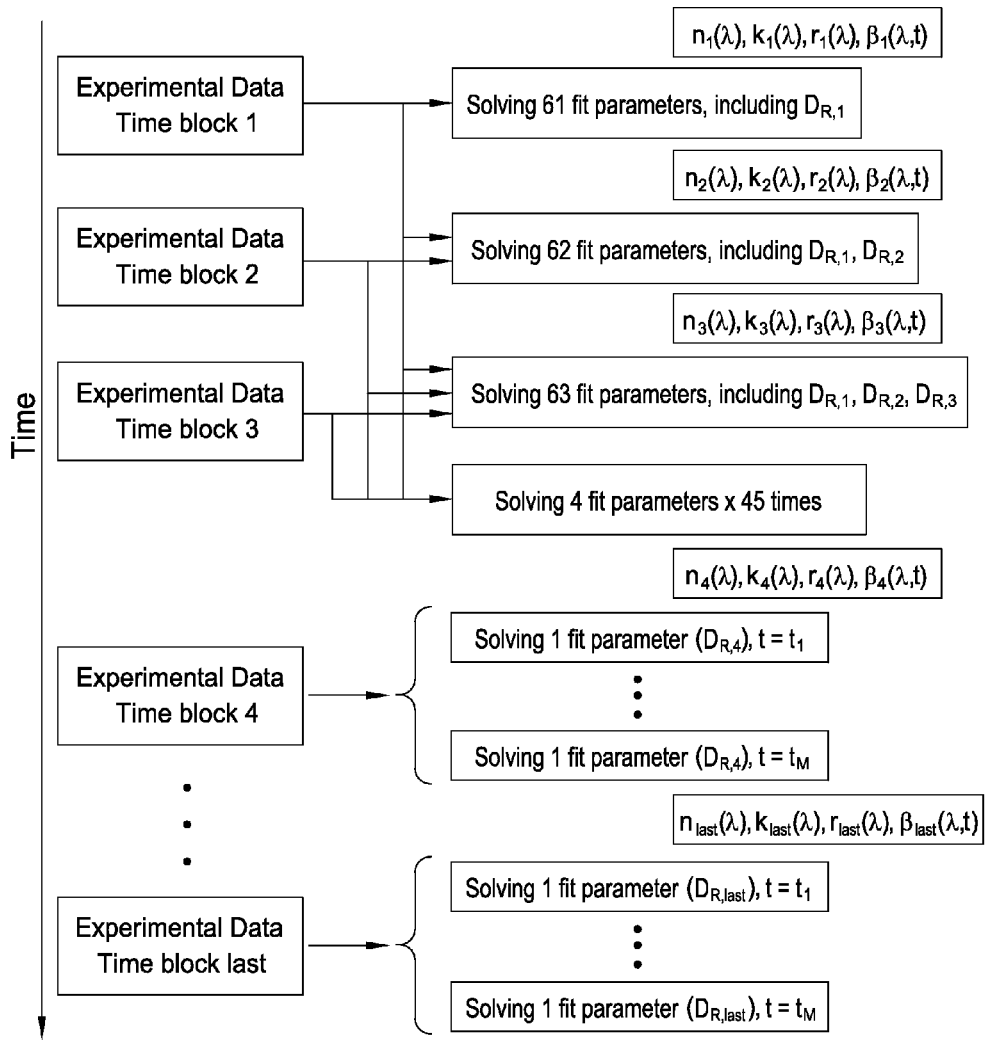
FIG. 13 is a flow diagram summarizing a method of determining layer thickness according to another embodiment.

This process is summarized in the flow diagram of FIG. 13.

An exemplary silicon oxide layer may be formed using any of the apparatus herein, as follows. A substrate is disposed on the substrate support of a processing chamber having the features described herein. A precursor gas mixture is formed by flowing TEOS at 1,000 mgm through a vaporizer and mixing with 5,000 sccm of helium and 6,000 sccm of N$_2$O. The gas mixture is flowed into the processing chamber. It should be noted that if a zoned showerhead is used, the TEOS may be flowed through one zone while the N$_2$O is flowed through the other zone. The helium flow may be split into two parts, a first part used to carry or dilute the vaporized TEOS into the first zone and a second part used to carry or dilute the N$_2$O into the second zone.

Pressure in the processing chamber is set to 4.0 Torr, spacing between the face plate of the chamber and the substrate is set to 400 mils. Face plate temperature is set to 200° C. Side wall tuning electrode current target is set to 6 A and substrate support tuning electrode current target is set to 1 A. Substrate temperature is set to 500° C. with offset between the temperature zones of the substrate support set to 5° C., with the outer zone at a higher temperature than the inner zone.

Power is coupled into the precursor gas to form a plasma. High frequency RF power at a frequency of 13.56 MHz is applied at 500 W of power, and low frequency RF power at a frequency of 300 kHz is applied at 100 W of power. The conditions are continued for a desired time to deposit a layer having a desired thickness, typically from 200 Å to 2,000 Å. The deposited silicon oxide layer has a thickness with a standard deviation that is no more than about 1%. Thus, the thickness uniformity of the deposited layer is no worse than about 1%.

A silicon oxide layer may be formed using silane as a precursor by another embodiment of the processes described herein using an apparatus described herein. Silane is flowed at 100 sccm, with helium at 3,000 sccm and N$_2$O at 6,000 sccm. Spacing is 300 mils, pressure is 3 Torr, high frequency power is at 400 W, low frequency power is at 100 W, face plate temperature is at 200° C., substrate temperature is 500° C., temperature zone offset is 5° C. (outer above inner), side wall tuning electrode current target is 1 A, substrate support tuning electrode current target is 3 A. A silicon oxide layer is formed with thickness uniformity that is no worse than about 1%.

A silicon nitride layer may be formed by another embodiment of the processes described herein using an apparatus described herein. Silane is flowed at 30 sccm, nitrogen gas at 3,000 sccm, ammonia gas at 6,000 sccm, and argon at 1,000 sccm. Spacing is 700 mils, pressure is 3 Torr, high frequency power is at 600 W, low frequency power is at 200 W, face plate temperature is at 200° C., substrate temperature is 500° C., temperature zone offset is 5° C. (outer above inner), side wall tuning electrode current target is 7 A, substrate support tuning electrode current target is 1 A. A silicon nitride layer is formed with thickness uniformity that is no worse than about 1%.

A silicon nitride layer may be formed by another embodiment of the processes described herein using an apparatus described herein. Silane is flowed at 150 sccm, nitrogen gas at 6,000 sccm, and ammonia gas at 1,000 sccm. Spacing is 700 mils, pressure is 4 Torr, high frequency power is at 600 W, low frequency power is at 200 W, face plate temperature is at 200° C., substrate temperature is 500° C., temperature zone offset is 5° C. (outer above inner), side wall tuning electrode current target is 6 A, substrate support tuning electrode current target is 1 A. A silicon nitride layer is formed with thickness uniformity that is no worse than about 1%.

A doped amorphous silicon layer may be formed by another embodiment of the processes described herein using an apparatus described herein. Silane is flowed at 500 sccm, helium at 10,000 sccm, and a dopant precursor such as TMB, borane, and/or phosphine, diluted to a concentration of 95% in helium, is flowed at 500 sccm. Spacing is 300 mils, pressure is 10 Torr, high frequency power is at 300 W, no low frequency power is applied, face plate temperature is at 175° C., substrate temperature is 500° C., temperature zone offset is 0° C., side wall tuning electrode current target is 6 A, substrate support tuning electrode current target is 3 A. A doped amorphous silicon layer is formed with thickness uniformity that is no worse than about 1%.

Stacks of layers such as the layers described above may be made sequentially by adjusting chamber conditions from one recipe to the next. Gas flows may be interrupted and the chamber purged between recipes, if desired to create sharp interfaces. Alternately, chamber conditions may be ramped from one recipe to the next while deposition is continued to make graded interfaces.

The in-situ monitoring algorithm described above may be used to monitor the thickness of each layer in a stack, for example an alternating stack of silicon oxide and silicon nitride, or an alternating layer of polysilicon and silicon oxide. In each case, as layers are deposited at the beginning of the stack, the algorithms utilizing reflectivity of the subjacent material are implemented so as to track changes in the subjacent layer reflectivity as layers are deposited.

It has been found that layer stacks including polysilicon layers may follow a simplified approach, due to the highly absorbing nature of polysilicon at shorter wavelengths. When forming a stack of alternating polysilicon and silicon oxide layers, for example, the subjacent layer reflectivity at wavelengths below about 600 nm has an observable effect up to three layers below the surface, but not beyond. In such a structure, the reflectivity spectrum taken from a stack of 10 alternating polysilicon/oxide layers is observed to overlay the spectrum taken from the same stack after the fourth pair of layers at wavelengths below about 600 nm. This same behavior is independent of the first layer (i.e. whether the first layer is polysilicon or oxide). Thus, one efficient approach includes fitting reflectivity data to a time-series model during deposition of the first three pairs of layers (the first six layers), after which the subjacent layer reflectivity may be assumed to be time-invariant at shorter wavelengths, and a wavelength series fit procedure may be used.

The invention claimed is:

1. A method of determining thickness of a layer during deposition of the layer on a subjacent layer of a substrate, comprising:
reflecting a broad spectrum radiation from the substrate;
analyzing the spectrum of the reflected light using a spectrograph;
fitting a Fresnel model to the analyzed spectrum based on refractive index and extinction coefficient of the layer being deposited, and based on thickness of the subjacent layer; and
determining optical properties of the subjacent layer and the layer thickness by minimizing the square of the difference between the analyzed spectrum and the model.

2. The method of claim 1, further comprising repeating the reflecting the broad spectrum radiation from the substrate, analyzing the reflected spectrum, and fitting the Fresnel model to monitor changes in the reflected spectrum, wherein the determining the optical properties is based on the changes in the reflected spectrum.

3. The method of claim 2, wherein the changes in the reflected spectrum include a period and a phase shift.

4. The method of claim 3, wherein layer thickness is determined from phase shift, and further comprising determining deposition rate from the period.

5. The method of claim 1, wherein minimizing the square of the difference between the analyzed spectrum and the model comprises determining a wavelength-dependent amplitude and phase that minimizes the square of the difference between the analyzed spectrum and the model.

6. The method of claim 5, wherein determining the wavelength-dependent amplitude and phase comprises defining an estimate and increment for each wavelength-dependent amplitude and phase.

7. A method of determining thickness of a layer during deposition of the layer on a subjacent layer of a substrate, comprising:
reflecting a broad spectrum radiation from the substrate;
analyzing the spectrum of the reflected light using a spectrograph;
fitting a Fresnel model to the analyzed spectrum based on refractive index and extinction coefficient of the layer being deposited, and based on thickness of the subjacent layer; and
determining optical properties of the subjacent layer and the layer thickness by repeated a process including minimizing the square of the difference between the analyzed spectrum and the model, wherein the process comprises:
determining a deposition rate from a subset of the reflected spectrum; and
determining the optical properties of the subjacent layer from the remainder of the reflected spectrum.

8. The method of claim 7, further comprising repeating the reflecting the broad spectrum radiation from the substrate, analyzing the reflected spectrum, and fitting the Fresnel model to monitor changes in the reflected spectrum, wherein the determining the optical properties is based on the changes in the reflected spectrum, and determining the optical properties of the subjacent layer is determined from a subset of the changes in the reflected spectrum.

9. The method of claim 8, wherein the changes in the reflected spectrum include a period and a phase shift.

10. The method of claim 9, wherein layer thickness is determined from phase shift, and further comprising determining deposition rate from the period.

11. The method of claim 7, wherein minimizing the square of the difference between the analyzed spectrum and the model comprises determining a wavelength-dependent amplitude and phase that minimizes the square of the difference between the analyzed spectrum and the model.

12. The method of claim 11, wherein determining the wavelength-dependent amplitude and phase comprises defining an estimate and increment for each wavelength-dependent amplitude and phase.

13. A method of determining thickness of a layer during deposition of the layer on a subjacent layer of a substrate, comprising:
repeatedly reflecting a broad spectrum radiation from the substrate to define a reflectivity at multiple time points;
analyzing the spectrum of the reflected light using a spectrograph;
fitting a Fresnel model to the analyzed spectrum based on refractive index and extinction coefficient of the layer being deposited, and based on thickness of the subjacent layer;
determining optical properties of the subjacent layer and the layer thickness by repeating a process including minimizing the square of the difference between the analyzed spectrum and the model, wherein the process comprises:
determining a first deposition rate from the reflectivity using a subset of the time points and a subset of the spectrum of the reflected light; and
determining optical properties of the subjacent layer using the subset of time points, the first deposition rate, and the remainder of the reflected spectrum; and
determining a second deposition rate using the determined optical properties of the subjacent layer.

14. The method of claim 13, wherein determining the second deposition rate is performed repeatedly using subsets of the time points.

15. The method of claim 13, wherein the Fresnel model includes a linear combination of the square of reflectivities in two orthogonal polarization directions.

16. The method of claim 13, wherein the optical properties of the subjacent layer include an amplitude and phase of wavelength-dependent reflectivity.

17. The method of claim 16, wherein determining the second deposition rate is performed repeatedly using subsets of the time points.

18. The method of claim 17, wherein the Fresnel model includes a linear combination of the square of reflectivities in two orthogonal polarization directions.

* * * * *

UNITED STATES PATENT AND TRADEMARK OFFICE
CERTIFICATE OF CORRECTION

PATENT NO.       : 9,157,730 B2
APPLICATION NO.  : 14/056203
DATED            : October 13, 2015
INVENTOR(S)      : Rajagopalan et al.

It is certified that error appears in the above-identified patent and that said Letters Patent is hereby corrected as shown below:

In Detailed Description:

Column 17, Line 19, please delete ""a"" and insert -- "α" -- therefor;

Column 17, Line 25, please delete ""a"" and insert -- "α" -- therefor;

Column 17, Line 29, please delete ""a"" and insert -- "α" -- therefor;

Column 18, Line 65, please delete ""n"" and insert -- "β" -- therefor;

Column 19, Line 1, please delete ""n"" and insert -- "β" -- therefor;

Column 21, Line 11, please delete "($\lambda$)" and insert -- $\phi(\lambda)$ -- therefor;

Column 21, Line 12, please insert -- . -- after shift;

Column 21, Line 14, please delete "$d = \lambda/4\pi n$.";

Column 25, Line 30, please delete "FP($\lambda$,t)" and insert -- $F^p(\lambda,t)$ -- therefor.

Signed and Sealed this
Twelfth Day of July, 2016

Michelle K. Lee
*Director of the United States Patent and Trademark Office*